United States Patent
Scott et al.

(10) Patent No.: US 11,547,871 B2
(45) Date of Patent: Jan. 10, 2023

(54) SYSTEMS AND METHODS FOR PERSONALIZED RADIATION THERAPY

(71) Applicant: CVERGENX, INC., St. Petersburg, FL (US)

(72) Inventors: Jacob G. Scott, Gates Mills, OH (US); Javier Torres-Roca, St. Petersburg, FL (US)

(73) Assignee: CVERGENX, INC., St. Petersburg, FL (US)

(*) Notice: Subject to any disclaimer, the term of this patent is extended or adjusted under 35 U.S.C. 154(b) by 319 days.

(21) Appl. No.: 16/658,961

(22) Filed: Oct. 21, 2019

(65) Prior Publication Data

US 2020/0121948 A1 Apr. 23, 2020

Related U.S. Application Data

(60) Provisional application No. 62/747,861, filed on Oct. 19, 2018.

(51) Int. Cl.
*A61N 5/10* (2006.01)
*C12Q 1/6883* (2018.01)

(52) U.S. Cl.
CPC ......... *A61N 5/1031* (2013.01); *C12Q 1/6883* (2013.01); *A61N 2005/1032* (2013.01); *C12Q 2600/158* (2013.01)

(58) Field of Classification Search
CPC .......... A61N 2005/1032; A61N 5/1031; C12Q 1/6883; C12Q 1/6886; C12Q 2600/106; C12Q 2600/158
See application file for complete search history.

(56) References Cited

U.S. PATENT DOCUMENTS

| | | | |
|---|---|---|---|
| 8,655,598 B2 | 2/2014 | Torres-Roca et al. | |
| 8,660,801 B2 | 2/2014 | Torres-Roca et al. | |
| 9,846,762 B2 | 12/2017 | Torres-Roca et al. | |
| 2009/0076734 A1 | 3/2009 | Torres-Roca et al. | |
| 2017/0283873 A1 | 10/2017 | Rico et al. | |

(Continued)

FOREIGN PATENT DOCUMENTS

| | | |
|---|---|---|
| WO | 2005044997 A2 | 5/2005 |
| WO | 2020082071 A1 | 4/2020 |

OTHER PUBLICATIONS

Eschrich et al. "Systems Biology Modeling of the Radiosensitivity Network: a Biomarker Discovery Platform" Oct. 1, 2009, Int. J. Radiat. Oncol. Biol. Phys. 75(2):497-505.

(Continued)

*Primary Examiner* — Mark R Gaworecki
(74) *Attorney, Agent, or Firm* — Troutman Pepper Hamilton Sanders LLP

(57) ABSTRACT

Disclosed herein are methods for personalized treatment of individual patient tumors. In one embodiment, a method of calculating a personalized radiation therapy dosage for a subject comprises determining expression levels of one or more signature genes from a subject's tumor sample, applying a linear regression model to the gene expression levels and assigning a radiation sensitivity index (RSI) to the subject's tumor sample, calculating a genomic adjusted radiation dose (GARD) value based on RSI, radiation dose and fractionation schedule of the subject, and calculating a personalized radiation dosage (RxRSI) for the subject based on a pre-determined GARD value.

24 Claims, 7 Drawing Sheets

A  Biological Heterogeneity - RSI

B  Individualized RT Clinical Effect - GARD

C  GARD-high patients have better LC

D  RxRSI — Personalized genomic RT dose

(56) References Cited

U.S. PATENT DOCUMENTS

2018/0148791 A1    5/2018  Scott et al.

OTHER PUBLICATIONS

International Search Report and Written Opinion for PCT/US2019/057230 dated Jan. 6, 2020.
Scott et al. "A Genome-based Model for Adjusting Radiotherapy dose (GARD): a Retrospective, Cohort-based Study" Feb. 2017, The Lancet Oncology 18(2):202-211.
Ahmed et al., "Radiosensitivity of Lung Metastases by Primary Histology and Implications for Stereotactic Body Radiation Therapy Using the Genomically Adjusted Radiation Dose," Journal of Thoracic Oncology (DATE) vol. 13, No. 8, pp. 1121-1127. (May 4, 2018).
Ahmed et al., "Utilizing the Genomically Adjusted Radiation Dose (GARD) to Personalize Adjuvant Radiotherapy in Triple Negative Breast Cancer Management," eBiomedicine (Aug. 12, 2019) vol. 47, pp. 163-169.
Baine et al., "Genome-Based Modeling for Adjusting Radiotherapy Dose (GARD)—a Significant Step Toward the Future of Personalized Radiation Therapy," Transl Cancer Res. Mar. 1, 2017; 6(Suppl 2): S418-S420.
Eschrich et al., "A Gene Expression Model of Intrinsic Tumor Radiosensitivity: Prediction of Response and Prognosis After Chemoradiation," International Journal of Radiation (Oct. 1, 2009); vol. 75, No. 2, pp. 489-496.
European Search Report for European Patent Application No. 19874381.7 dated Jul. 5, 2022.
Torres-Roca et al., "A Molecular Assay of Tumor Radiosensitivity: A Roadmap Towards Biology-Based Personalized Radiation Therapy," Personalized Medicine (Jul. 1, 2012); vol. 9, No. 5, pp. 1-17.
Scott et al., "A genome-based model for adjusting radiotherapy dose (GARD): a retrospective, cohort-based study," Lancet Oncol. Feb. 2017;18(2):202-211.

US 11,547,871 B2

SYSTEMS AND METHODS FOR PERSONALIZED RADIATION THERAPY

CLAIM OF PRIORITY

This application claims priority to U.S. Provisional Application No. 62/747,861 filed on Oct. 19, 2018 titled "SYSTEMS AND METHODS FOR PERSONALIZED RADIATION THERAPY" and is incorporated herein by reference.

SUMMARY

Disclosed herein are systems and methods for personalized treatment of individual patient tumor. In one embodiment, a method of calculating a personalized radiation therapy dosage for a subject comprises:

determining expression levels of one or more signature genes from a subject's tumor sample;

applying a linear regression model to the gene expression levels and assigning a radiation sensitivity index (RSI) to the subject's tumor sample;

calculating a genomic adjusted radiation dose (GARD) value based on RSI, radiation dose and fractionation schedule of the subject; and calculating a personalized radiation dosage (RxRSI) for the subject based on a pre-determined GARD value.

In an additional embodiment, a method of treating a subject having a tumor comprises:

determining expression levels of one or more signature genes from a subject's tumor sample;

applying a linear regression model to the gene expression levels and assigning a radiation sensitivity index (RSI) to the subject's tumor sample;

calculating genomic adjusted radiation dose (GARD) value based on RSI, radiation dose and fractionation schedule of the subject;

calculating a personalized radiation dosage (RxRSI) for the subject based on a pre-determined GARD value; and administering the calculated personalized radiation dosage (RxRSI) to the subject.

In a further embodiment, a system for developing a personalized radiation therapy treatment plan for a subject having a tumor comprises:

a processor; and a memory operably coupled to the processor, the memory having computer-executable instructions stored thereon that, when executed by the processor, cause the processor to:

determine a radiation sensitivity index (RSI) of the tumor from expression levels of one or more signature genes in the tumor;

determine a genomic adjusted radiation dose (GARD) value based on RSI, radiation dose and fractionation schedule of the subject;

calculate a personalized radiation dosage (RxRSI) for the subject based on a pre-determined GARD value;

calculate the normal tissue toxicity of the personalized radiation dosage; and provide the personalized radiation therapy treatment plan for the subject.

DETAILED DESCRIPTION

Figure 1:
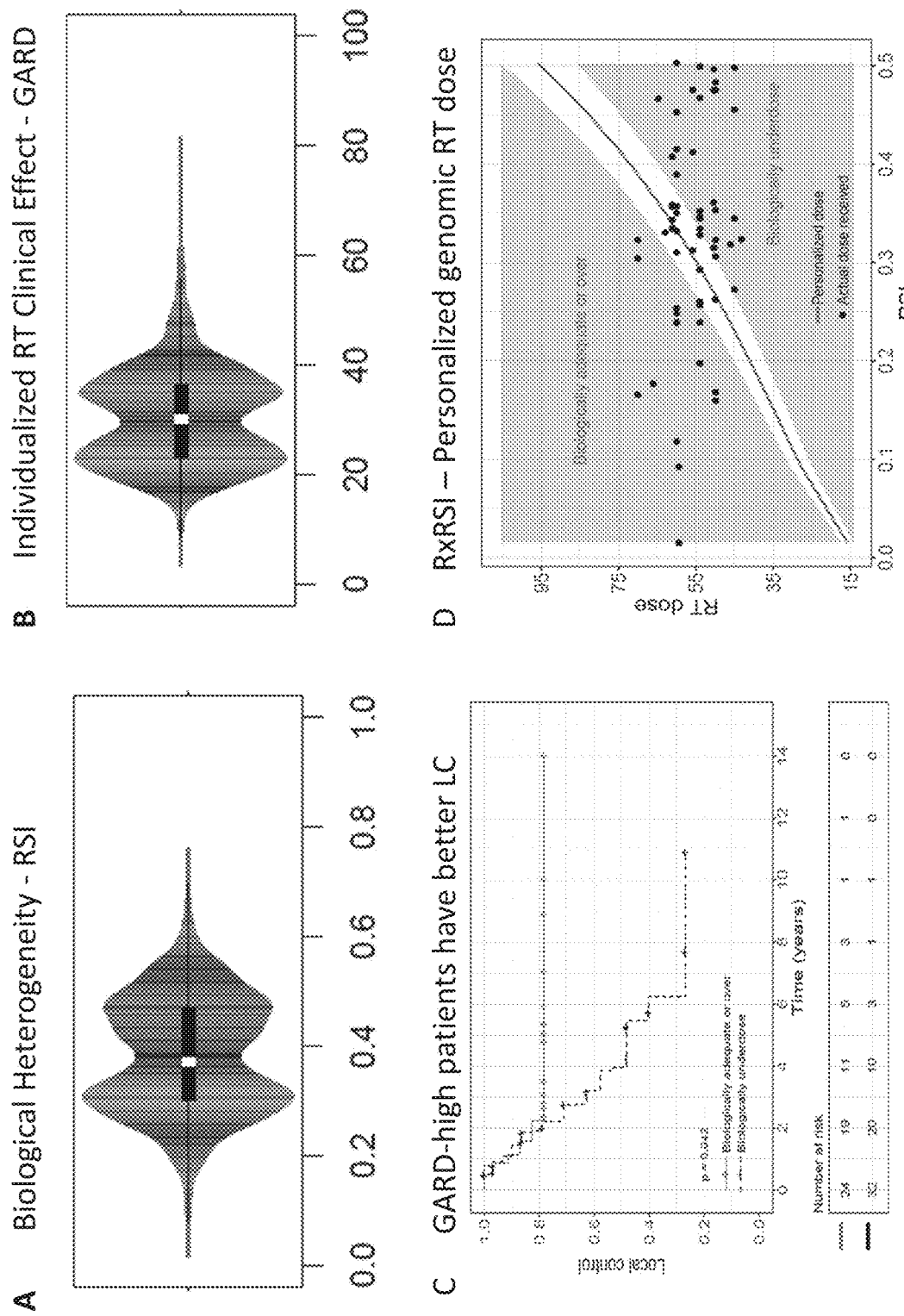
FIG. 1 depicts RxRSI, a novel system to calculate a biologically optimized personalized radiation dose. (A) shows RSI values for 1,747 non-small lung cancer samples from TCC. The distribution demonstrates a bimodal peak in RSI value. (B) shows GARD values for these samples assuming that they received 60 Gy (n=30, d=2), a standard dose used for non-small cell lung cancer patients. The application of a uniform RT dose to a biological heterogeneous population results in a non-uniform clinical effect which GARD represents. Similar to the RSI distribution, GARD shows heterogeneity of clinical effect with a bimodal distribution (GARD range 8.6 to 72.8). (C) shows patients that achieved a GARD value of 33 or above from empiric dosing in the Moffitt lung cancer clinical cohort have superior local control to patients whose GARD value is below 33. (D) shows personalized RT dose or RxRSI as the physical dose required to achieve a GARD value of 33. The RxRSI for each of the 60 patients in the Moffitt lung cancer clinical cohort were calculated. The RxRSI for each patient is represented by the blue line in the graph (range—15.71-95.94). The actual empiric dose received by each patient is marked by the dots.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Unless defined otherwise, all technical and scientific terms used herein have the same meanings as commonly understood by one of ordinary skill in the art. Although any methods and materials similar or equivalent to those described herein can be used in the practice or testing of embodiments disclosed, the preferred methods, devices, and materials are now described.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

The term "patient" and "subject" are interchangeable and may be taken to mean any living organism which may be treated with compounds of the present invention. As such, the terms "patient" and "subject" may include, but are not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "treating" is used herein, for instance, in reference to methods of treating a skin disorder or a systemic condition, and generally includes the administration of a compound or composition or a therapy regimen which reduces the frequency of, or delays the onset of, symptoms of a medical condition. This can include reversing, reducing, or arresting the symptoms, clinical signs, and underlying pathology of a condition in a manner to improve or stabilize a subject's condition.

Radiation therapy (RT) is the medical use of radiation to treat malignant cells, such as cancer cells. This radiation can have an electromagnetic form, such as a high-energy photon, or a particulate form, such as an electron, proton, neutron, or alpha particle. By far, the most common form of radiation used in practice today is high-energy photons. Photon absorption in human tissue is determined by the energy of the radiation, as well as the atomic structure of the tissue in question. The basic unit of energy used in radiation oncology is the electron volt (eV); $10^3$ eV=1 keV, $10^6$ eV=1 MeV. At therapeutic energies, the three major interactions between photons and tissue are the photoelectric effect, Compton effect, and pair production.

Due to biological heterogeneity, radiation therapy (RT) does not uniformly work on all tissue samples, and a uniform "one-size fits all" RT dose for a given cancer-type may not be ideal. Therefore, there remains a need for personalized radiation dose planning methods and systems.

Disclosed herein are methods for personalized treatment of individual patient tumors. In one embodiment, a method of calculating a personalized radiation therapy dosage for a subject comprises:

determining expression levels of one or more signature genes from a subject's tumor sample;

applying a linear regression model to the gene expression levels and assigning a radiation sensitivity index (RSI) to the subject's tumor sample;

calculating a genomic adjusted radiation dose (GARD) value based on RSI, radiation dose and fractionation schedule of the subject; and calculating a personalized radiation dosage (RxRSI) for the subject based on a pre-determined GARD value.

In an additional embodiment, a method of treating a subject having a tumor comprises:

determining expression levels of one or more signature genes from a subject's tumor sample;

applying a linear regression model to the gene expression levels and assigning a radiation sensitivity index (RSI) to the subject's tumor sample;

calculating genomic adjusted radiation dose (GARD) value based on RSI, radiation dose and fractionation schedule of the patient;

calculating a personalized radiation dosage (RxRSI) for the subject based on a pre-determined GARD value; and administering the calculated personalized radiation dosage (RxRSI) to the subject.

In some embodiments, any method known in the art may be used for obtaining a tumor sample from a subject. The tumor sample may comprise at least one living cell (preferably a plurality of cells), e.g., a cell from a tumor (e.g., from a biopsy), a normal cell, or a cultured cell. Commonly used methods to obtain tumor cells include surgical (the use of tissue taken from the tumor after removal of all or part of the tumor) and needle biopsies. The samples should be treated in any way that preserves intact the gene expression levels of the living cells as much as possible, e.g., flash freezing or chemical fixation, e.g., formalin fixation. Any method known in the art can be used to extract material, e.g., protein or nucleic acid (e.g., mRNA) from the sample. For example, mechanical or enzymatic cell disruption can be used, followed by a solid phase method (e.g., using a column) or phenol-chloroform extraction, e.g., guanidinium thiocyanate-phenol-chloroform extraction of the RNA. A number of kits are commercially available for use in isolating mRNA. Purification can also be used if desired.

In some embodiments, the tumor is a cancer tumor selected from colorectal cancer, breast cancer, ovarian cancer, pancreatic cancer, head and neck cancer, bladder cancer, liver cancer, renal cancer, melanoma, gastrointestinal cancer, prostate cancer, small cell lung cancer, non-small cell lung cancer, sarcoma, glioblastoma, T-cell lymphoma, B-cell lymphoma, endometrial cancer, and cervical cancer.

In some embodiments, any method known in the art may be used to determine the gene expression levels in a tumor sample. Gene expression levels can be determined in many different ways including the quantification of fluorescence of hybridized mRNA on glass slides, Northern blot analysis, real-time reverse transcription PCR (RT-PCR), microarray or other measures of gene expression abundance.

In some embodiments, the methods include determining expression levels of signature genes in one or more cells of a tumor. In some embodiments, the methods include determining the expression levels of a plurality of signature genes, e.g., two, three, four, five, six, seven, eight, nine, or all ten signature genes, as follows: androgen receptor (AR); jun oncogene (c-Jun); signal transducer and activator of transcription 1 (STAT1); protein kinase C, beta (PKCb); V-rel reticuloendotheliosis viral oncogene homolog A (RELA or p65); c-Ab1 oncogene 1 (c-Ab1); small ubiquitin-like modifier 1 (SUMO1); p21 activated kinase-2 (PAK2); histone deacetylase 1 (HDAC1); and interferon regulatory factor 1 (IRF1).

In some embodiments, the methods include determining expression levels of signature genes in one or more cells of a tumor, and determining a radiation sensitivity index (RSI) of the tumor based on the expression levels of the signature genes. To determine the RSI, the methods described herein may use a rank-based linear algorithm.

In some embodiments, determining a radiation sensitivity index of a tumor comprises applying a linear regression model to the gene expression levels, e.g., a rank-based linear regression model. In some embodiments, the expression levels of the plurality of signature genes are weighted. A linear regression model useful in the methods described herein includes gene expression levels and coefficients, or weights, for combining expression levels. The coefficients can be calculated using a least-squares fit of the proposed model to a measure of cellular radiation sensitivity. The functional form of the algorithm is given below, where each of the $k_i$ coefficients will be determined by fitting expression levels to a particular RSI measure:

$$RSI = k_1 * AR + k_2 * c\text{-}jun + k_3 * STAT1 + k_4 * PKC + k_5 * RelA + k_6 * cAb1 + k_7 * SUMO1 + k_8 * PAK2 + k_9 * HDAC + k_{10} * IRF1$$

Further methods and embodiments for determining radiation sensitivity index (RSI) are described in U.S. Pat. Nos. 8,660,801; 9,846,762; and 8,655,598, which are incorporated herein by reference.

As described herein, RSI provides an indication of whether radiation therapy is likely to be effective in treating the subject's tumor. RSI has a value approximately between 0 and 1 (Eschrich et al., Systems biology modeling of the radiosensitivity network: a biomarker discovery platform, Int. J. Radiat. Oncol. Biol. Phys. (2009)). It should be understood that assigning RSI according to the linear regression model of gene expression levels described in U.S. Pat. Nos. 8,660,801; 9,846,762; and 8,655,598, is provided only as an example and that other known techniques for assigning radiation sensitivity can optionally be used with the systems and methods described herein.

In some embodiments, the method further comprises calculating the Genomic Adjusted Radiation Dose (GARD) for each tumor sample, and is described in U.S. patent application Ser. No. 15/571,617 which incorporated herein by reference. GARD is derived using the linear quadratic (LQ) model, the individual RSI and the radiation dose and fractionation schedule for each patient as follows:

The LQ model in its simplest form is represented by: $S = e - nd(\alpha + \beta d)$, where n is the number of fractions of radiation, d is the dose per fraction, and $\alpha$ and $\beta$ represent the linear and quadratic radiosensitivity parameters, respectively.

Since RSI is a molecular estimate of SF2 in cell lines (survival fraction at 2 Gy), a patient-specific $\alpha$ is derived by substituting RSI for Survival (S) in the equation above, where dose (d) is 2 Gy, n=1 and $\beta$ is a constant ($0.05/Gy^2$). GARD is calculated using the classic equation for biologic effect shown by equation $E = nd(\alpha + \beta d)$, the patient-specific $\alpha$ and the radiation dose and fractionation received by each patient. Additionally, the GARD value can be predictive of tumor recurrence in the subject after treatment.

In some embodiments, the method comprises calculating a personalized radiation dosage (RxRSI) for each individual tumor or subject based on a pre-determined GARD value. The personalized radiation dose or RxRSI is the physical dose required to achieve a pre-determined GARD value. The RxRSI is calculated using the formula below:

$$RxRSI = GARD \text{ target value}/(\alpha + \beta d),$$

where alpha is calculated based on the patient's RSI as described above and beta is a constant ($0.05/Gy^2$).

In some embodiments, a pre-determined GARD value may be calculated based on improved outcome in a particular cancer type. In other embodiments, a pre-determined GARD value may be calculated based on empiric values for a cancer type.

The pre-determined GARD value may vary depending on the cancer type. For example, the pre-determined GARD value for a subject suffering from non-small cell lung cancer is 33. In some embodiments, the pre-determined GARD value for other cancers may be more or less than 33, such as any number between 2 and 150.

The empirical radiation dose for a solid epithelial tumor ranges from 60 to 80 Gy, while lymphomas are treated with 20 to 40 Gy. For example, lung cancers are treated between 60 and 74Gy, prostate cancers are generally treated between 37.25 to 80 Gy, and esophageal cancers are treated between 44 to 70 Gy. It is possible that the empirical dose that the patients receive is lower or higher than what they need. A personalized radiation dose would be ideal to achieve an improved outcome.

In some embodiments, the personalized radiation dose that is calculated may be 5% less than the empirical dosing value, may be 10% less than the empirical dosing value, may be 15% less than the empirical dosing value, may be 20% less than the empirical dosing value, may be 25% less than the empirical dosing value, may be 30% less than the empirical dosing value, may be 35% less than the empirical dosing value, may be 40% less than the empirical dosing value, may be 50% less than the empirical dosing value, or may be 60% less than the empirical dosing value.

In some embodiments, the personalized radiation dose that is calculated may be 5% more than the empirical dosing value, may be 10% more than the empirical dosing value, may be 15% more than the empirical dosing value, may be 20% more than the empirical dosing value, may be 25% more than the empirical dosing value, may be 30% more than the empirical dosing value, may be 35% more than the empirical dosing value, may be 40% more than the empirical dosing value, may be 50% more than the empirical dosing value, or may be 60% more than the empirical dosing value.

In some embodiments, radiation is administered in at least about 1 Gray (Gy) fraction at least once every other day to a treatment volume. In some embodiments, radiation is administered in at least about 2 Gy fractions at least once per day to a treatment volume. In some embodiments, radiation is administered in at least about 2 Gy fractions at least once per day to a treatment volume for five consecutive days per week. In another embodiment, radiation is administered in 3 Gy fractions every other day, three times per week to a treatment volume. In yet another embodiment, a total of at least about 20 Gy, about 30 Gy, about 40 Gy, about 50 Gy, about 60 Gy, about 70 Gy, about 80 Gy, about 90 Gy, or about 100 Gy of radiation is administered to a subject in need thereof.

The methods disclosed herein may be practiced in an adjuvant setting. "Adjuvant setting" refers to a clinical setting in which an individual has a history of a proliferative disease, particularly cancer, and generally (but not necessarily) has been treated with therapy, which includes, but is not limited to, surgery and/or chemotherapy. However, because of a history of the proliferative disease, these individuals are considered at risk of developing that disease or may harbor detectable and/or microscopic disease. Treatment or administration in the "adjuvant setting" refers to a subsequent mode of treatment.

The methods provided herein may also be practiced in a "neoadjuvant setting," that is, the method may be carried out before the primary/definitive therapy. In some aspects, the individual has previously been treated. In other aspects, the individual has not previously been treated. In some aspects, the treatment is a first line therapy.

In some embodiments, any of the methods of treatment of RT described herein can be administered in combination with one or more additional therapies to the individual, such as surgery and/or chemotherapy. In some embodiments, various classes of chemotherapeutic agents can be administered in combination with RT. Non-limiting examples include: alkylating agents (e.g. cisplatin, carboplatin, or oxaliplatin), antimetabolites (e.g., azathioprine or mercaptopurine), anthracyclines, plant alkaloids (including, e.g. vinca alkaloids (such as, vincristine, vinblastine, vinorelbine, or vindesine) and taxanes (such as, paclitaxel, taxol, or docetaxel)), topoisomerase inhibitors (e.g., camptothecins, irinotecan, topotecan, amsacrine, etoposide, etoposide phosphate, or teniposide), podophyllotoxin (and derivatives thereof, such as etoposide and teniposide), and other antineoplastics (e.g., dactinomycin, doxorubicin, epirubicin, bleomycin, mechlorethamine, cyclophosphamide, chlorambucil, or ifosfamide).

In some embodiments, a radiation therapy treatment disclosed herein may be combined with other targeted therapies, such as immunoconjugates or antibodies coupled to cytotoxic agents. Non-limiting cytotoxic agents that can be coupled to an antibody include a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

Also disclosed herein are systems and methods for developing a personalized radiation therapy treatment plan for a subject having a tumor. In some embodiments, the system comprises:
 a processor; and
 a memory operably coupled to the processor, the memory having computer-executable instructions stored thereon that, when executed by the processor, cause the processor to:
  determine a radiation sensitivity index (RSI) of the tumor from expression levels of one or more signature genes in the tumor;
  determine a genomic adjusted radiation dose (GARD) value based on RSI, radiation dose and fractionation schedule of the patient;
  calculate a personalized radiation dosage (RxRSI) for the subject based on a pre-determined GARD value;
  calculate the normal tissue toxicity of the personalized radiation dosage; and
  provide the personalized radiation therapy treatment plan for the subject.

In some embodiments, the system comprises a processor and a memory operably coupled to the processor, the memory having computer-executable instructions stored thereon that, when executed by the processor, cause the processor to provide a personalized radiation therapy treatment plan for the subject based on one or more of the following input:
 a radiation sensitivity index (RSI) of the tumor from expression levels of one or more signature genes in the tumor;
 a genomic adjusted radiation dose (GARD) value based on RSI, radiation dose and fractionation schedule of the patient;
 a personalized radiation dosage (RxRSI) for the subject based on a pre-determined GARD value; and
 the normal tissue toxicity of the personalized radiation dosage.

In some embodiments, the system comprises a processor and a memory operably coupled to the processor, the memory having computer-executable instructions stored thereon that, when executed by the processor, cause the processor to:
  calculate a personalized radiation dosage (RxRSI) for the subject based on a pre-determined GARD value;
  calculate the normal tissue toxicity of the personalized radiation dosage; and provide the personalized radiation therapy treatment plan for the subject.

In some embodiments, the system comprises a processor and a memory operably coupled to the processor, the memory having computer-executable instructions stored thereon that, when executed by the processor, cause the processor to provide the personalized radiation therapy treatment plan for the subject based on:
 personalized radiation dosage (RxRSI) for the subject; and
 the normal tissue toxicity of the personalized radiation dosage.

In some embodiments, the method includes integrating the prescribed RT dosage into a commercially available radiation treatment planning system that generates personalized treatment plan based on the patient's RSI, GARD and RxRSI values. The methods disclosed herein can be implemented in digital electronic circuitry, or in computer software, firmware, or hardware, or in combinations of them.

Accordingly, as discussed herein, various embodiments may include non-transitory computer-readable media for analyzing health information. In particular, some embodiments may have a health/diagnosis analysis system configured to analyze, examine, search, investigate, consider, evaluate, and/or otherwise process health information and to generate various medical assessments based on the health information. Non-limiting examples of medical assessments include medical diagnoses, medical orders, and/or risk assessments. Health information, as used herein, may include any type of information associated with the health or physical characteristics of a patient, including, but not limited to, name, address, age, gender, demographic information, weight, height, medications, surgeries and other medical procedures (e.g., diagnostic tests, diagnostic imaging tests, or the like), occupation(s), past and current medical conditions, family history, patient description of health condition, healthcare professional description of health condition, and/or symptoms.

In some embodiments, the analysis process may involve accessing health information associated with a patient and providing a medical assessment based on various analyses of the health information. In some embodiments, the health information analysis system may receive input from a healthcare provider concerning the accuracy, completeness, correctness, or other measure of a medical assessment for use in determining future medical assessments.

The systems and devices described herein provide multiple technological advantages on current processes and techniques. One non-limiting technological advantage is that the health information analysis system may provide medical assessments to healthcare professionals based on a patient's full medical history, including across healthcare providers and information platforms. Such analyses are generally not possible using conventional processes and technology because, for instance, they would require a great deal of time to be effective and practical when providing healthcare to patients.

Another non-limiting technological advantage may be that the health information analysis system is capable of dynamically adapting its analysis processes based on healthcare professional feedback, updated information, or the like. A further non-limiting technological advantage is that the health information analysis system may present timely and dynamically updated information to medical professionals in a format that is readily comprehensible to provide a timely analysis, including in real-time or substantially real-time. The presentation of health information according to some embodiments allows medical professionals to provide more efficient and effective healthcare to patients compared with conventional techniques and processes that are generally paper-based or use limited graphical user interfaces (GUI) that are not capable of providing a comprehensive and meaningful picture of a patient's health information.

In some embodiments, the information, or data, acquired by the system may generally include all information collected or generated prior to the medical procedure. Thus, for example, information about the patient may be acquired from a patient intake form or electronic medical record (EMR). Examples of patient information that may be collected include, without limitation, patient demographics, diagnoses, medical histories, progress notes, vital signs, medical history information, allergies, and lab results. The data may also include images related to the patient's area of interest. It should be understood, that the images may be captured using any known or future medical imaging device, for example, Magnetic Resonance Imaging (MRI), Computed Tomography (CT), X-ray, ultrasound, or any other modality known in the art. The data may also comprise quality of life data captured from the patient. For example, in one embodiment, a patient may use a software application ("app") to answer one or more questionnaires regarding their current quality of life. In a further embodiment, the health information may include demographic, anthropometric, cultural, or other specific traits about a patient that can coincide with activity levels and specific patient activities to customize the surgical plan to the patient. For example, certain cultures or demographics may be more likely to perform a repetitive physical task or be exposed to a particular set of environmental factors.

In a further embodiment, the computer system may refine or improve the diagnosis by adjusting weighted factors and/or modifying one or more determination factors based on outcome data. For example, an embodiment may utilize, a closed loop algorithm to perform statistical and machine learning modeling. In certain implementations, the outcome data may include overall survival information, progression-free survival information, response rate to a specific drug, and/or other similar outcome data.

For example, a procedure for refining weights can involve testing a variety of statistical and machine learning modeling techniques and selecting the one that performs best. For a given set of medical procedures, multiple models may be trained to predict the outcomes. The best model can be selected, or a combination and/or averaging of the best models may be newly generated. In certain implementations, rules can be in place to determine what alterations are made to the system.

Accordingly, the algorithm/system as described herein may include machine learning and/or other similar statistical-based modeling techniques. For example, the algorithm used may depend on an expected outcome. For example, a processing device can be configured to use a first process or algorithm to calculate refinements to a derived diagnosis based upon a first set of outcome data while also using a second or different algorithm to calculate refinements. Different methods and algorithms may be used to calculate the refined weights in concert or substantially simultaneously. The output of each of the different methods and algorithms can then be compared/further analyzed to determine which output is highest rated, or the output of each method and algorithm can be combined into a combinational metric.

In some embodiments, the personalized radiation dosage (RxRSI) may be calculated using a computer program product. The computer program product may include a computer readable storage medium (or media) having computer readable program instructions thereon for causing a processor to carry out aspects of the present invention.

The computer readable storage medium can be a non-transitory tangible device that can retain and store instructions for use by an instruction execution device (e.g., one or more processors). The computer readable storage medium may be, for example, but is not limited to, an electronic, magnetic, optical, electromagnetic, semiconductor storage device, or any suitable combination of the foregoing. A non-exhaustive list of more specific examples of the computer readable storage medium includes the following: a portable computer diskette, a head disk, random access memory (RAM), read-only memory (ROM), erasable programmable read-only memory (EPROM or Flash memory), static random access memory (SRAM), a compact disc read-only memory (CD-ROM), a digital versatile disk (DVD), a memory stick, a floppy disk, a mechanically encoded device such as punch-card(s) or raised structures in a groove having instructions recorded thereon, and/or any suitable combination of the foregoing.

A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein may be downloaded to respective computing/processing devices from a computer readable storage medium or to an external computer or external storage device via a network, for example, the Internet, a local area network (LAN), a wide area network (WAN), and/or a wireless network. The network may comprise conductive transmission cables (e.g., copper cables), optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

The processor can process instructions for execution within the computing device, including instructions stored in the memory. The processor can also include separate analog and digital processors. The processor can provide, for example, coordination of the other components of the device, such as the user interface, applications, and wireless communication.

The processor may communicate with a user through a control interface and/or a display interface coupled to a display. The display can be, for example, a TFT LCD display, an OLED display, or other appropriate display technology. The display interface can comprise appropriate circuitry for driving the display to present graphical and other information to a user. The control interface can receive commands from a user and convert them for submission to the processor. In addition, an external interface can be in communication with processor, so as to enable near area communication of device with other devices.

In some embodiments, the system includes computer software that integrates information for each individual patient including imaging, genomic and clinical data (i.e. clinical prescription). The system generates a conventional standard of care (SoC) treatment plan as well as a personalized treatment plan that incorporates the individual patient RSI, GARD, RxRSI, and normal tissue toxicity. The physician can then evaluate both plans and choose which one to use for the patient based on standard dose-volume histogram (DVH) metrics of normal tissue and tumor coverage.

In some embodiments, a computer-implemented method for minimizing the risk of radiation therapy is provided. The method comprises:
  obtaining a radiation sensitivity index (RSI) of a subject's tumor from expression levels of one or more signature genes in the tumor;
  determining a genomic adjusted radiation dose (GARD) value based on RSI, radiation dose and fractionation schedule of the subject;
  calculating a personalized radiation dosage (RxRSI) for the subject based on a pre-determined GARD value;
  calculating normal tissue toxicity of the personalized radiation dosage; and
  providing a personalized radiation therapy treatment plan for the subject.

Figure 7:
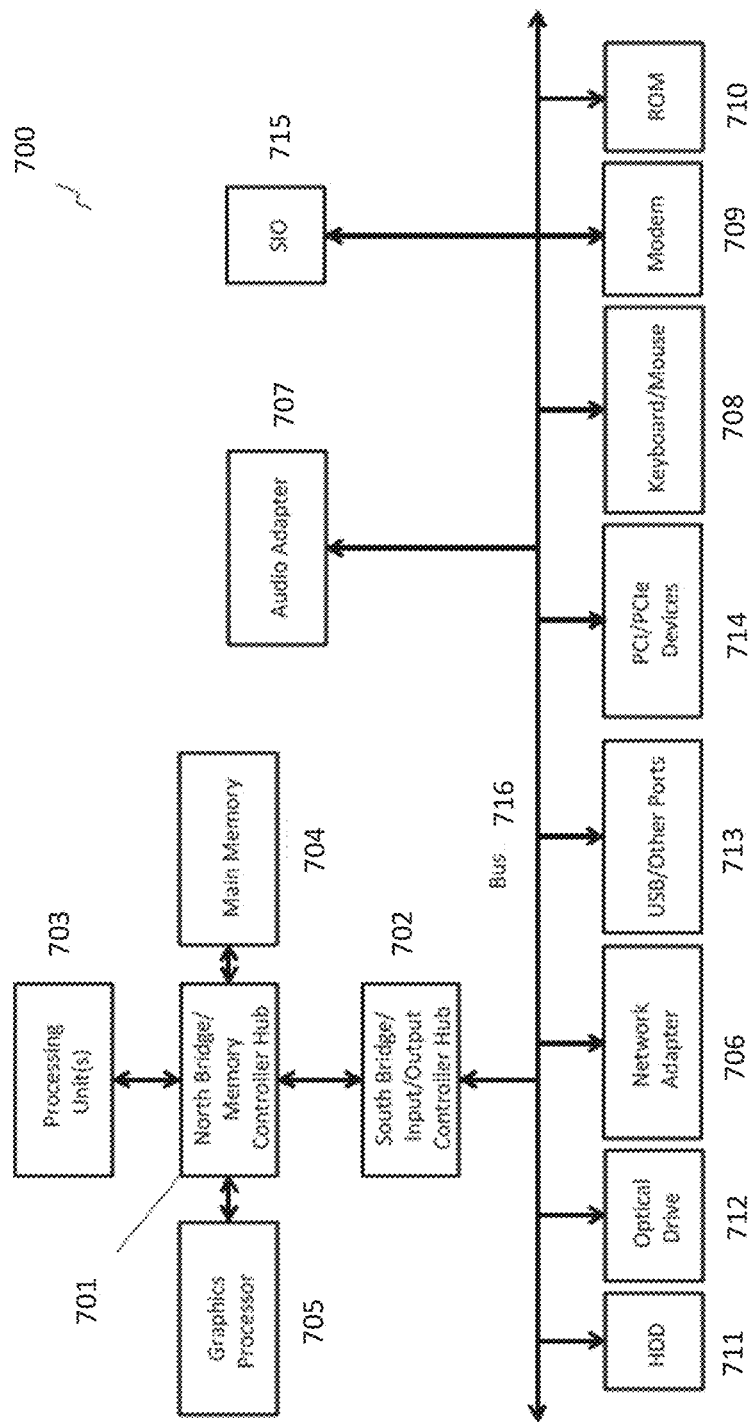
FIG. 7 illustrates a block diagram of an illustrative data processing system according to an embodiment.

FIG. 7 illustrates a block diagram of an illustrative data processing system 700 in which aspects of the illustrative embodiments are implemented. The data processing system 700 is an example of a computer, such as a server or client, in which computer usable code or instructions implementing the process for illustrative embodiments of the present invention are located. In some embodiments, the data processing system 700 may be a server computing device. For example, data processing system 700 can be implemented in a server or another similar computing device operably connected to a surgical system. The data processing system 700 can be configured to, for example, transmit and receive information related to a patient and/or a related surgical plan with the surgical system.

In the depicted example, data processing system 700 can employ a hub architecture including a north bridge and memory controller hub (NB/MCH) 701 and south bridge and input/output (I/O) controller hub (SB/ICH) 702. Processing unit 703, main memory 704, and graphics processor 705 can be connected to the NB/MCH 701. Graphics processor 705 can be connected to the NB/MCH 701 through, for example, an accelerated graphics port (AGP).

In the depicted example, a network adapter 706 connects to the SB/ICH 702. An audio adapter 707, keyboard and mouse adapter 708, modem 709, read only memory (ROM) 710, hard disk drive (HDD) 711, optical drive (e.g., CD or DVD) 712, universal serial bus (USB) ports and other communication ports 713, and PCI/PCIe devices 714 may connect to the SB/ICH 702 through bus system 716. PCI/PCIe devices 714 may include Ethernet adapters, add-in cards, and PC cards for notebook computers. ROM 710 may be, for example, a flash basic input/output system (BIOS). The HDD 711 and optical drive 712 can use an integrated drive electronics (IDE) or serial advanced technology attachment (SATA) interface. A super I/O (SIO) device 715 can be connected to the SB/ICH 702.

An operating system can run on the processing unit 703. The operating system can coordinate and provide control of various components within the data processing system 700. As a client, the operating system can be a commercially available operating system. An object-oriented programming system, such as the Java™ programming system, may run in conjunction with the operating system and provide calls to the operating system from the object-oriented programs or applications executing on the data processing system 700. As a server, the data processing system 700 can be an IBM® eServer™ System® running the Advanced Interactive Executive operating system or the Linux operating system. The data processing system 700 can be a symmetric multiprocessor (SMP) system that can include a plurality of processors in the processing unit 703. Alternatively, a single processor system may be employed.

Instructions for the operating system, the object-oriented programming system, and applications or programs are located on storage devices, such as the HDD 711, and are loaded into the main memory 704 for execution by the processing unit 703. The processes for embodiments described herein can be performed by the processing unit 703 using computer usable program code, which can be located in a memory such as, for example, main memory 704, ROM 710, or in one or more peripheral devices.

A bus system 716 can be comprised of one or more busses. The bus system 716 can be implemented using any type of communication fabric or architecture that can provide for a transfer of data between different components or devices attached to the fabric or architecture. A communication unit such as the modem 709 or the network adapter 706 can include one or more devices that can be used to transmit and receive data.

Those of ordinary skill in the art will appreciate that the hardware depicted in FIG. 7 may vary depending on the implementation. Other internal hardware or peripheral devices, such as flash memory, equivalent non-volatile memory, or optical disk drives may be used in addition to or in place of the hardware depicted. Moreover, the data processing system 700 can take the form of any of a number of different data processing systems, including but not limited to, client computing devices, server computing devices, tablet computers, laptop computers, telephone or other communication devices, personal digital assistants, and the like. Essentially, data processing system 700 can be any known or later developed data processing system without architectural limitation.

EXAMPLES

Example 1: Personalizing Radiotherapy Prescription Dose Using Genomic Markers of Radiosensitivity The empiric basis of radiation therapy (RT), the most commonly utilized therapeutic agent in clinical oncology, has gone unmodified for over 70 years. RT is prescribed based on a uniform, one-size fits all approach, delivering small daily doses of RT over several weeks (i.e. fractionation). This fractionation approach is based on studies performed in rams and rabbits by Regaud, Schinz and Slotopolsky over 100 years ago. And the standard total doses for control of sub-clinical, microscopic and macroscopic disease (50, 60 and 70 Gy) were established in the 1960s based on tumor control probability models for head and neck cancer patients.

The linear quadratic (LQ) model has been a stalwart in the field that has informed RT dose and fractionation since originally proposed by Catcheside and Lea in the 1940s. The LQ proposes that radiation response is a two parameter function of dose delivered (one parameter, alpha, is linear in dose, and the other, beta, is quadratic). Of note, it has been utilized to calculate equivalent dose and fractionation regimens that have been shown to be safe and effective in clinical trials. However, a fundamental limitation of the LQ model is that it assumes that tumor biology is homogenous and that all individuals in a population have a similar opportunity to benefit from RT, with differences in response being related to probabilistic events. Thus, the LQ model predicted that uniform RT dose escalation would result in significant clinical gains across multiple disease sites. Unfortunately, multiple prospective Phase 3 randomized trials have recently disproven this prediction.

The development of "omic" technologies has revealed that cancer is the most heterogeneous and complex disease that affects humans. The era of precision medicine is focused on the identification of parameters that drive biological heterogeneity. Rather than a single disease with a uniform treatment, the complexity and diversity of cancer requires many treatment options that are matched and optimized based on the patient's individual tumor biology.

Although RT remains a critical curative agent for cancer, it has yet to adapt a biological basis in the clinic. It was previously proposed that the gene expression-based radiosensitivity index (RSI), a surrogate for intrinsic cellular radiosensitivity, and the genomic-adjusted radiation dose (GARD), an individualized quantitative metric of the clinical effect of RT, could serve as the first approach to biology-based RT. Both RSI and GARD have been validated in multiple clinical cohorts and disease sites as a predictor of clinical outcome in patients treated with RT. Importantly, the Lancet Oncology commission identified GARD as a research priority in the field of radiation oncology. In addition, a recent independent study from Lund University provides corroborative evidence that RSI is predictive of RT benefit in breast cancer; a predictive biomarker.

It is hypothesized that, given the known heterogeneity of cancer, the current empiric basis for clinical dose and fractionation is a sub-optimal strategy to determine RT dose for a given individual patient. Indeed, assuming that the same dose of RT is optimal for every patient is inconsistent with the biologic principles of precision medicine because, theoretically, a single dose may under treat or over treat all patients. In this disclosure, the RSI/GARD model is utilized to calculate a personalized RT prescription that is informed by each individual patient's biology within a cohort of lung cancer patients treated with standard empiric RT dose at Moffitt Cancer Center. The personalized RT prescription which is termed as RxRSI represents the prescription dose needed for each patient to achieve a GARD value associated with optimal local control. With this information in hand, it is able to quantify for each patient, the likely under or over-dosing compared to predicted optimal prescription dose (RxRSI).

To quantify the penalties of over- and under-dosing, a precision RT model was developed which estimates local control based on whether an optimal RT dose is delivered and then penalizes that outcome based on exposure to excess normal tissue complication risk (penalized local control, pLC). Critically, the precision RT model is validated by demonstrating that it correctly predicts the lack of local control benefit derived from uniform dose escalation in lung cancer demonstrated in RTOG 0617. Finally, the precision RT model estimates that personalized prescription RT dose may improve the local control in lung cancer by an absolute 6.3% when compared to standard empiric RT dose. Further, it is shown within current standard of care dosing how radiation dose optimization can be achieved through biologically selected dose-escalation, enabling personalized medicine to enter radiation oncology clinics today.

Materials and Methods

Lung Cancer Modeling Cohort—

This cohort was extracted from Total Cancer Care (TCC), a prospective IRB-approved data and tissue collection protocol active at Moffitt and 18 other institutions since 2006. Tumors from patients enrolled in the TCC protocol were arrayed on Affymetrix Hu-RSTA-2a520709 (Affymetrix, Santa Clara, Calif.), which contains approximately 60,000 probe sets representing 25,000 genes. Chips were normalized using iterative rank-order normalization (IRON). Batch-effects were reduced using partial-least squares (PLS). The normalized, de-batched expression values for 1,747 NSCNC (NSCLC) samples and the ten RSI-genes were extracted from the TCC database.

Lung Cancer Clinical Cohort—

This cohort has been previously described. It includes a total of 60 patients with Stage 3 NSCLC treated at Moffitt with post-operative RT (dose range 45-70 Gy). All patients in the cohort were consented for the TCC protocol and had genomic data available. The microarray data was normalized using the robust multiple-array average (RMA). The clinical endpoint was local control. The median follow up (based on the reverse Kaplan-Meier method) in censored patients free from local failure was 59.5 months (95% CI:38.0-68.5 months).

Radiosensitivity Index (RSI)—

RSI scores for the TCC modeling cohort and lung cancer clinical cohort dataset were previously generated. RSI was previously trained in 48 cancer cell lines to predict cellular radiosensitivity as determined by survival fraction at 2 Gy (SF2). Each of ten genes in the algorithm is ranked based on gene expression (highest expressed gene is ranked at 10 and lowest at 1), and RSI is calculated using the pre-determined equation:

$$RSI = -0.0098009*AR + 0.0128283*cJun + 0.0254552*STAT1 - 0.0017589*PKC - 0.0038171*RelA + 0.1070213*cABL - 0.0002509*SUMO1 - 0.0092431*PAK2 - 0.0204469*HDAC1 - 0.0441683*IRF1.$$

Genomic Adjusted Radiation Dose (GARD)—

GARD has been previously described. Briefly, it is derived using the LQ model, the individual RSI and the radiation dose/fractionation schedule for each patient. First, a patient-specific $\alpha$ is derived by substituting RSI for Survival (S) in the LQ equation below where dose (d) is 2Gy, n=1 and $\beta$ is a constant ($0.05/Gy^2$):

$$S = e^{-nd(\alpha + \beta d)}.$$

GARD is calculated using the classic equation for biologic effect, GARD=nd ($\alpha + \beta d$), and using the patient-specific $\alpha$ is calculated as stated above, and the number of fractions (n) and dose per fraction (d) received by each patient. A GARD cut-point of 33 was previously identified and published for the lung clinical cohort.

Biologically-Optimized Personalized RT Dose (RxRSI)—

RxRSI is the physical dose required to achieve a previously identified GARD threshold (GARD≥33). RxRSI is calculated using the following formula:

$$RxRSI = 33/(\alpha + \beta d)$$

where alpha is calculated based on the patient's RSI as described above and beta is a constant ($0.05/Gy^2$).

When comparing RxRSI to the empiric dose received by patients in the lung cancer clinical cohort, the RxRSI and empiric dose were defined as matched if they were within 10% of each other. As GARD was developed based on standard fractionation, it was assumed that RxRSI is delivered in a similar manner (i.e. dose per fraction is ~2Gy).

Genomic Radiation Treatment Planning—

Figure 4:
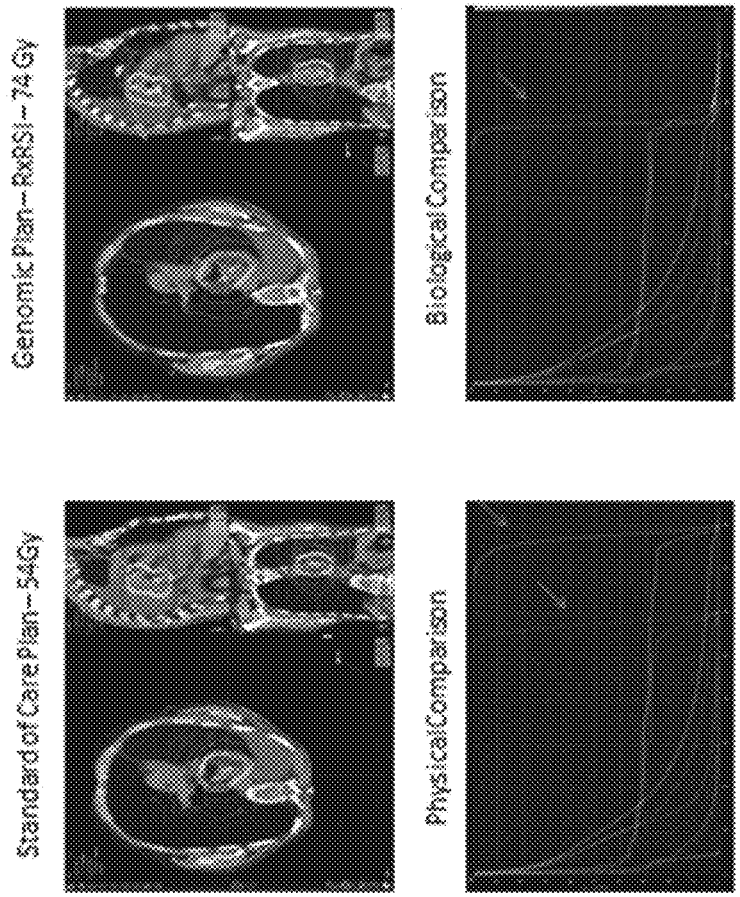
FIG. 4 shows that optimizing and personalizing RT dose with RSI/GARD. A genomic radiation treatment plan was developed by integrating the algorithms for RSI, GARD and RxRSI into a commercially-available RT treatment planning system. The system integrates imaging, biological and prescription information and generates a standard plan based on empiric dosing and an alternative genomic radiation plan based on the patient's RSI, GARD and RxRSI. The actual treatment plans used to treat the Moffitt lung cancer clinical cohort were not retrievable. However, the clinical prescription utilized, the genomic data and clinical outcome were retrievable from the TCC database. A set of de-identified radiation treatment plans was created for post-operative RT in lung cancer. Five base plans were selected that represented common treatment areas in a post-operative lung, including central lesions, right and left-sided lesions as well as larger and smaller fields. 6 different plans were created for each of the five base plans to represent different biological conditions requiring RxRSIs within the range observed in the cohort (48 Gy, 54 Gy, 62 Gy, 74 Gy, 88 Gy, 95 Gy). (A, B) shows standard of care and genomic plan for a patient receiving post-operative RT. (C, D) shows standard dose plan was prescribed to 54 Gy. Genomic planning calculates the RxRSI in this example as 74 Gy.

To develop a treatment plan to biologically optimize RT for individual patients, the algorithms and equations that define RSI, GARD, and RxRSI were integrated into radiation treatment planning software. The software integrates information for each individual patient including imaging, genomic and clinical data (i.e. clinical prescription). The system generates a conventional standard of care (SoC) treatment plan as well as a genomic treatment plan that incorporates the individual patient RSI, GARD and RxRSI (FIG. 4).

Figure 5:
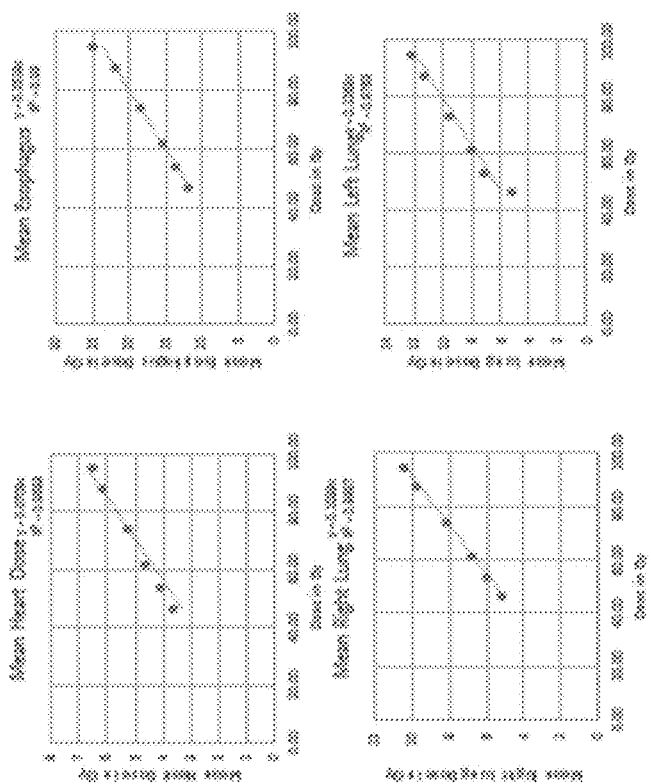
FIG. 5 shows a linear model to estimate the impact of RT dose adjustment and normal tissue dose. Using the plans generated, the mean dose was calculated to each normal tissue target across all 30 genomic plans. A linear model was generated by plotting dose to PTV vs mean dose to each of the normal tissues. The resulting linear equation was utilized to calculate an approximate mean dose to normal tissue on a per gray basis.

To quantify the potential clinical impact of genomic radiation treatment planning, and to represent the diversity of plans observed in clinical practice, plans with both right and left-sided large targets, central targets and one with a small peripheral target were selected. Six different biological conditions requiring six different RxRSIs (48 Gy, 54 Gy, 62 Gy, 74 Gy, 88 Gy, 95 Gy) were assumed and a total of 30 radiation plans using the Eclipse treatment planning system (Varian Medical Systems, Inc., Palo Alton, Calif.) and standard dosimetric approaches were generated. Dosimetric parameters for normal tissue including mean heart dose, mean esophagus dose, and mean right and left lung dose were calculated for all genomic plans (Tables 2-5). In general, the esophagus (V76) became the main dose limiting structure, particularly for plans above 74 Gy. The resulting data was utilized to generate a linear model to estimate the impact of dose personalization on normal tissue (FIG. 5).

Linear Model for Normal Tissue Estimates—

The mean dose to each normal tissue target (heart, left lung, right lung and esophagus) was calculated across the 30 genomic plans developed. Mean normal tissue dose was plotted against PTV prescription dose to obtain a Pearson's correlation coefficient for mean heart, left lung, right lung, and esophageal dose ($R^2$: 0.98, 0.99, 0.97, 0.99, respectively). These linear equations were then used to calculate an approximate mean dose to normal tissue on a per gray basis for modeling studies.

Normal Tissue Toxicity—

Calculations for relative risk for a given dose received or dose adjustment was accomplished using different methods for each tissue site, depending on the available data and recommendations in the literature. When possible, data on the rate of complication per dose received or a quantitative NTCP model which has the benefit of flexibility in choosing dosing parameters was used. For generalizability, specific dose-toxicity endpoints were not referenced.

In the QUANTEC review of lung complications, the primary endpoint is radiation pneumonitis. The reviewers conducted a meta-analysis of applicable studies and performed logistic regression on rates of radiation pneumonitis versus mean lung dose as follows, $$p = \frac{\exp(b_0 + b_1 \cdot MLD)}{1 + \exp(b_0 + b_1 \cdot MLD)}.$$

Parameters for b0 and b1 were calculated for a model in the above form.

The QUANTEC reported recommendations for toxicity endpoints for the esophagus were inconclusive due to the volume-dependent effect of the available data. Two of the studies, both published in 2005, provided quantitative models in the form of the Lyman-Kutcher-Burman equation, with parameters m and $TD_{50}$ that were within bounds of the confidence intervals, $$NTCP = \frac{1}{\sqrt{2\pi}} \int_{-\infty}^{t} e^{-x^2/2} dx.$$

Here $$t = \frac{EUD - TD_{50}}{m \times TD_{50}},$$

Cardiac complications due to radiation were modeled as a fixed rate of 7.4% increased risk per 1 Gy dose received by the heart. The endpoint included coronary events as defined by myocardial infarction, coronary revascularization, or death from ischemic heart disease.

Precision RxRSI Model—

Figure 2:
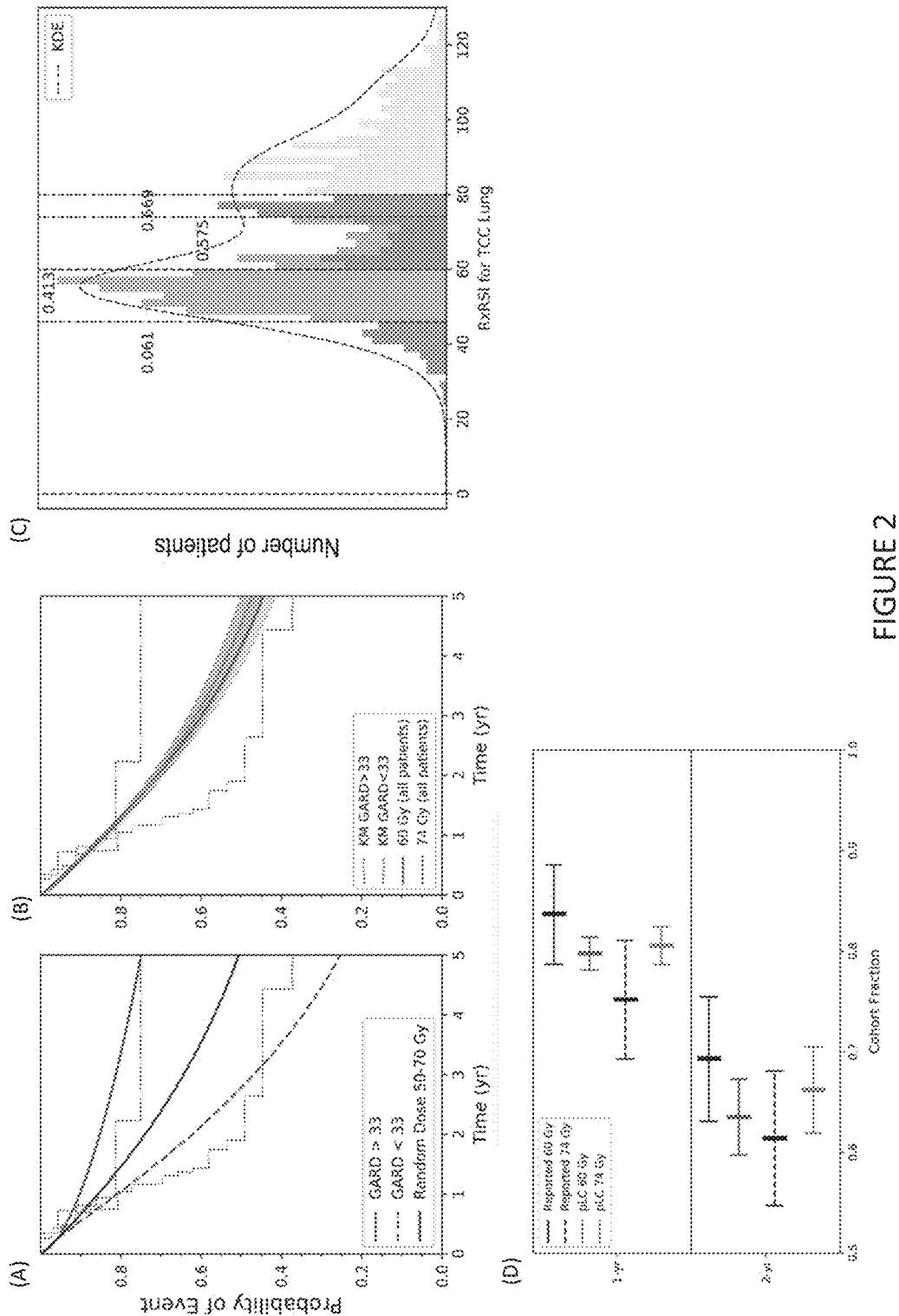
FIG. 2 depicts a Precision RxRSI model. (A) shows that precision RxRSI reproduces the clinical outcome observed in the Moffitt clinical cohort. It also depicts the probability of local control after initial treatment with patients differentiated by having a GARD score greater than or less than 33, respectively. This is demonstrated by the top and bottom curves. The middle curve shows the probability of local control for all patients receiving a random dose within the current standard of care range of 50-70 Gy. The KM curves for the Moffitt clinical cohort are also represented in the figure. (B) shows in silico clinical trial comparing predicted outcomes for simulated patients treated uniformly to 60 or 74 Gy similar to RTOG 0617. The precision RxRSI model predicts uniform dose escalation to 74 Gy would result in no improvement of pEFS. (C) shows a distribution of RxRSI for the lung TCC modeling cohort (n=1,747). 41% of patients are biologically-optimized at 60 Gy, and an additional 16% of patients are optimized by increasing the dose to 74 Gy. Over 40% of patients are undertreated at 74 Gy according to the precision RxRSI model. (D) shows a comparison of results from the pLC model and recently reported RTOG 0617 with overlapping confidence intervals.

The clinical cohort was divided into two groups based on the previously identified and published cut-point for GARD in the lung clinical cohort (GARD≥33 vs. GARD<33). Kaplan-Meier curves were fit for each group, as well as Weibull survival-type so that continuous survival and hazard functions could be applied more generally in further analysis. Next, outcomes under a random radiotherapy dosing regimen were estimated, under which each patient would receive a randomly selected radiotherapy dose between 50 and 70 Gy. This dose was then compared to the patient's individual RxRSI in order to determine probability of local control. The survival function for this dosing strategy was constructed as a linear combination of the initial two curves, with coefficients weighted by the fractional number of patients in that group. These survival curves are shown in FIG. 2A.

Validation of the Precision RxRSI Precision Model: In Silico Modelling of RTOG 0617—

Figure 6:
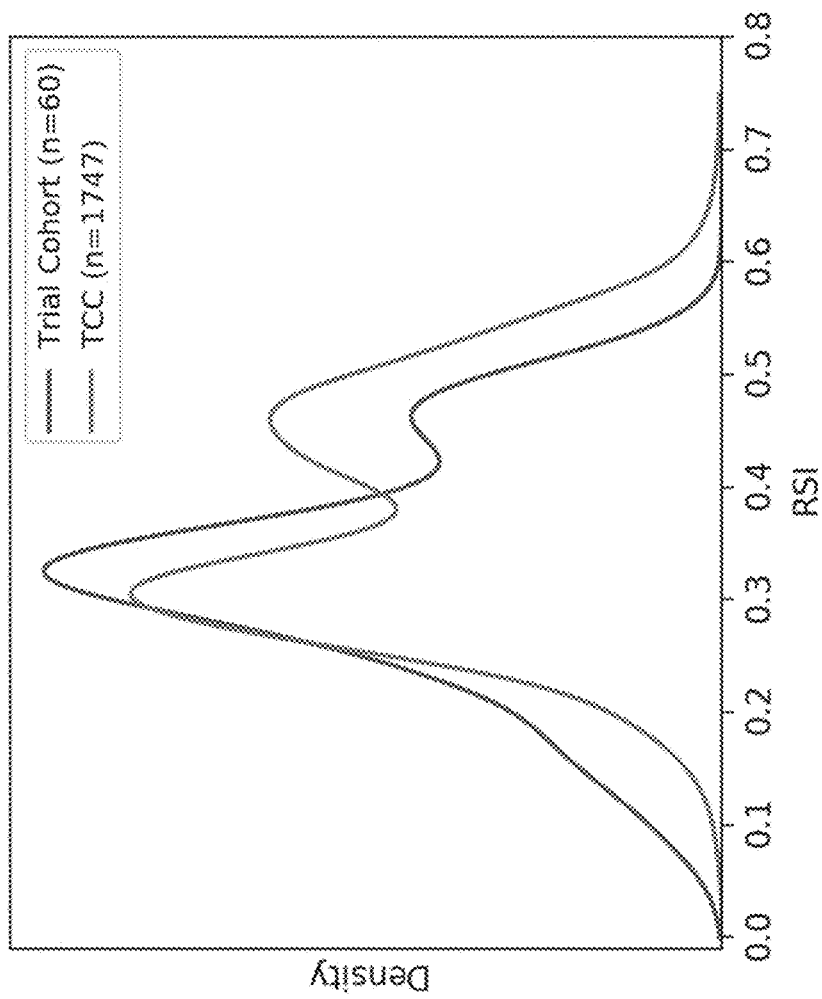
FIG. 6 shows RSI distribution for the Moffitt clinical cohort (n=60) and the TCC modeling cohort (n=1,747). Both distributions are statistically similar using Anderson-Darling and Kolmogorov-Smirnov tests, p<0.001.

To validate the precision RxRSI model, the results of the recently reported trial of dose escalation (60Gy vs 74Gy) in NSCLC were modeled. To understand the combined contributions of tumor and excess normal tissue effects on outcomes, penalized local control (pLC) was calculated, which includes local recurrence and events related to RT-related toxicity, but does not account for death due to disease progression or other causes. To calculate this curve, 1000 iterations of the following algorithm were completed: from an empiric distribution of 1747 NSCLC patients with measured RSI (from the Moffitt TCC cohort), which was statistically indistinguishable from the smaller 60 patient cohort reported above (p<<0.001 using Anderson-Darling and Kolmogorov-Smirnov tests, FIG. 6), at random, 207 patients for a 74Gy arm, and 217 patients for a 60Gy arm were selected. RxRSI was then calculated for each patient and this was compared to the dose received, and the patient was assigned to the appropriate GARD group for LC. The penalized local control curve was then modelled as $S(t)=C_1 S_1(t)+C_2 S_2(t)$, where $C_1$=fraction of patients with GARD≥33 and $C_2$=fraction of patients with GARD<33. Finally the survival curve for the 74Gy group was adjusted for the predicted hazard ratios in order to compare pLC for the two groups:

$$pLC(t)=[S_{74Gy}(t)]^{\overline{HR}_C \cdot \overline{HR}_E \cdot \overline{HR}_P}$$

where $\overline{HR}_C$, $\overline{HR}_E$, $\overline{HR}_P$ are the risks for each adverse outcome due to the increased dose from 60 to 74 Gy (cardiac, esophagitis, pneumonitis, respectively).

Statistical Methods—

Kaplan-Meier curves were generated to compare local control of patients that achieved a GARD of 33 or above from empirical dosing with that of patients whose GARD was below 33. A log rank test was used to compare the local control between GARD groups, with the level of significance set at 0.05 level.

Results

An approach to personalize RT prescription dose based on individual tumor biology FIG. 1 shows a feasible clinical approach to personalize RT prescription dose based on biological heterogeneity. First, the significant biological heterogeneity that the gene expression-based radiosensitivity index estimates in lung cancer patients from the TCC cohort is shown in FIG. 1A. As shown, there is a bimodal distribution of RSI scores across this population, suggesting that a uniform, one-size fits all approach to RT dose is sub-optimal for the majority of patients. Next, the distribution of the genomic adjusted radiation dose (GARD) that results from the clinical application of uniform RT dose (60 Gy) to the TCC population is shown in FIG. 1B. As expected, a uniform one-size fits all approach to RT prescription results in large differences in RT clinical effect between individuals (GARD range 8.6 to 72.8). As previously demonstrated, patients in the Moffitt lung cancer clinical cohort (n=60) who achieve a GARD>33 when empirically treated have an improved local control (FIG. 1C, 5-year LC, 78% vs. 48%, p=0.04). Finally, the personalized RT dose or RxRSI as the physical dose required to achieve a GARD value of 33 is defined. In FIG. 1D, the calculated RxRSI for the range of RSI values represented in the cohort (blue line) compared with the actual dose received by each patient in the cohort is shown. It is proposed that patients that achieve a GARD of 33 are biologically optimized in regards to tumor dose (blue region).

Current empiric RT prescription dose does not optimize radiotherapy dose at an individual level Next, RxRSI was generated for every patient in the Moffitt clinical cohort, which is summarized in Table 1 (RxRSI range 15.71-95.94). The clinical cohort could be divided in four groups. Group 1 patients (15/60, Table 2) were those where the prescribed empiric dose and the calculated RxRSI were within 10% of one another, which is considered as optimized. Group 2, which represented 50% of the patients (30/60), received a lower dose by more than 10% than the estimated RxRSI, suggesting that these patients received less than an optimal dose (Tables 3 and 4) and could benefit from personalized dose escalation. Group 2 could be sub-divided into subgroup 2a and 2b based on whether their estimated RxRSI was within the previously defined standard of care dose range (50-70 Gy as defined by NCCN for post-operative RT for NSCL cancer). For Group 2a, (15/60), the estimated RxRSI was within the standard of care for post-operative lung RT (50-70 Gy) as defined by NCCN (Table 3). Thus, these patients could have received their target RxRSI dose without varying the prescribed RT dose outside the standard of care range. For patients in Group 2b, the RxRSI was above the range considered standard of care (RxRSI>70Gy, Table 4), suggesting that moderate personalized dose escalation would not allow for optimization of their radiation related outcome.

TABLE 1

Generating RxRSI: Biological Optimization of Individual Treatment Plans Using Genomic Radiation Therapy Planning

| Group | Mean dose | Mean RSI | Mean GARD | Mean RxRSI | Mean dose diff (dose − RxRSI) |
|---|---|---|---|---|---|
| Group 1 (n = 15) | 58.4 | 0.3 | 33 | 58.5 | −0.5 |
| Group 2A (n = 15) | 50.67 | 0.33 | 27.74 | 60.35 | −9.68 |
| Group 2B (n = 15) | 54.43 | 0.46 | 20.95 | 86.68 | −32.25 |
| Group 3 (n = 15) | 60.19 | 0.20 | 53.52 | 50.92 | 9.27 |

TABLE 2

Group 1 sub-cohort. In these patients, the dose delivered and the calculated RxRSI matched.

| Patient ID | Actual dose | RSI | GARD | RxRSI | Actual vs RxRSI Dose Δ | Mean Esophageal Δ @ RxRSI | Mean Left Lung Δ @ RxRSI | Mean Right Lung Δ @ RxRSI | Mean Heart Δ @ RxRSI | Δ number treatment weeks (rounded up to whole fraction) |
|---|---|---|---|---|---|---|---|---|---|---|
| 46 | 54 | 0.26 | 36.378 | 48.986 | −5.014 | −1.263 | −0.633 | −0.551 | −0.355 | −1 |
| 47 | 60 | 0.31 | 35.126 | 56.369 | −3.631 | −0.914 | −0.459 | −0.399 | −0.257 | −0.8 |
| 48 | 60 | 0.31 | 35.126 | 56.369 | −3.631 | −0.914 | −0.459 | −0.399 | −0.257 | −0.2 |
| 49 | 63 | 0.33 | 34.885 | 59.596 | −3.404 | −0.857 | −0.43 | −0.374 | −0.241 | −1 |
| 50 | 61.2 | 0.334 | 33.522 | 60.246 | −0.954 | −0.24 | −0.12 | −0.105 | −0.068 | −0.6 |
| 51 | 50 | 0.262 | 33.453 | 49.323 | −0.677 | −0.171 | −0.086 | −0.074 | −0.048 | 0 |
| 52 | 54 | 0.292 | 33.192 | 53.688 | −0.312 | −0.079 | −0.039 | −0.034 | −0.022 | −0.6 |
| 53 | 60 | 0.332 | 33.088 | 59.841 | −0.159 | −0.04 | −0.02 | −0.018 | −0.011 | 0 |
| 54 | 61.2 | 0.343 | 32.711 | 61.74 | 0.54 | 0.136 | 0.068 | 0.059 | 0.038 | −0.6 |
| 55 | 55.8 | 0.312 | 32.464 | 56.721 | 0.921 | 0.232 | 0.116 | 0.101 | 0.065 | −0.4 |
| 56 | 61.2 | 0.357 | 31.538 | 64.038 | 2.838 | 0.715 | 0.358 | 0.312 | 0.201 | −0.2 |
| 57 | 60 | 0.35 | 31.493 | 62.87 | 2.87 | 0.723 | 0.363 | 0.315 | 0.204 | 0.4 |
| 58 | 61.2 | 0.358 | 31.406 | 64.306 | 3.106 | 0.782 | 0.392 | 0.341 | 0.22 | −0.2 |
| 59 | 60 | 0.357 | 30.884 | 64.111 | 4.111 | 1.035 | 0.519 | 0.452 | 0.291 | 0.6 |
| 60 | 54 | 0.328 | 30.107 | 59.189 | 5.189 | 1.307 | 0.655 | 0.57 | 0.368 | 0 |
| Mean | 58.4 | 0.3 | 33 | 58.5 | 0.1 | 0 | 0 | 0 | 0 | −0.307 |

TABLE 3

Group 2a patients. In this group, patients received lower dose by more than 10% than the calculated RxRSI. Adjustment of these patients dose could be done within standard of care range (50-70 Gy).

| Patient ID | Actual dose | RSI | GARD | RxRSI | Actual vs RxRSI Dose Δ | Mean Esophageal Increase @ RxRSI | Mean Left Lung Increase @ RxRSI | Mean Right Lung Increase @ RxRSI | Mean Heart Increase @ RxRSI | Increase number treatment weeks (rounded up to whole fraction) |
|---|---|---|---|---|---|---|---|---|---|---|
| 16 | 45 | 0.272 | 29.265 | 50.744 | 5.744 | 1.446 | 0.725 | 0.631 | 0.407 | 1 |
| 17 | 50 | 0.306 | 29.597 | 55.749 | 5.749 | 1.448 | 0.726 | 0.632 | 0.408 | 1.2 |
| 18 | 50.4 | 0.315 | 29.112 | 57.131 | 6.731 | 1.695 | 0.85 | 0.74 | 0.477 | 0.2 |
| 19 | 46 | 0.318 | 26.33 | 57.654 | 11.654 | 2.934 | 1.472 | 1.281 | 0.826 | 1.2 |
| 20 | 50 | 0.323 | 28.26 | 58.387 | 8.387 | 2.112 | 1.059 | 0.922 | 0.595 | 2 |
| 21 | 43.2 | 0.324 | 24.371 | 58.496 | 15.296 | 3.852 | 1.932 | 1.681 | 1.084 | 1.2 |
| 22 | 54 | 0.328 | 30.107 | 59.189 | 5.189 | 1.307 | 0.655 | 0.57 | 0.368 | 0 |
| 23 | 54 | 0.334 | 29.577 | 60.249 | 6.249 | 1.573 | 0.789 | 0.687 | 0.443 | 0.2 |
| 24 | 45 | 0.345 | 23.965 | 61.965 | 16.965 | 4.272 | 2.143 | 1.864 | 1.203 | 1.2 |
| 25 | 54 | 0.345 | 28.757 | 61.967 | 7.967 | 2.006 | 1.006 | 0.876 | 0.565 | 0.2 |
| 26 | 54 | 0.346 | 28.638 | 62.225 | 8.225 | 2.071 | 1.039 | 0.904 | 0.583 | 1.4 |
| 27 | 54 | 0.353 | 28.152 | 63.3 | 9.3 | 2.342 | 1.175 | 1.022 | 0.659 | 0.4 |
| 28 | 50 | 0.353 | 26.014 | 63.428 | 13.428 | 3.381 | 1.696 | 1.476 | 0.952 | 1.4 |
| 29 | 50.4 | 0.361 | 25.669 | 64.794 | 14.394 | 3.624 | 1.818 | 1.582 | 1.021 | 1 |
| 30 | 60 | 0.389 | 28.293 | 69.983 | 9.983 | 2.514 | 1.261 | 1.097 | 0.708 | 1 |
| Mean | 50.667 | 0.334 | 27.74 | 60.351 | 9.684 | 2.438 | 1.223 | 1.064 | 0.687 | 0.907 |

TABLE 4

Group 2b patients. Similar to group 2a patients, these patients received lower doses than the RxRSI. However dose adjustments for these patients are outside the standard of care and in many cases result in plans that do not meet DVH guideline criteria at our institution

| Patient ID | Actual dose | RSI | GARD | RxRSI | Actual vs RxRSI Dose Δ | Mean Esophageal Increase @ RxRSI | Mean Left Lung Increase @ RxRSI | Mean Right Lung Increase @ RxRSI | Mean Heart Increase @ RxRSI | Increase number treatment weeks (rounded up to whole fraction) |
|---|---|---|---|---|---|---|---|---|---|---|
| 31 | 61.2 | 0.407 | 27.475 | 73.507 | 12.307 | 3.099 | 1.554 | 1.353 | 0.873 | 0.6 |
| 32 | 55.8 | 0.412 | 24.731 | 74.458 | 18.658 | 4.698 | 2.357 | 2.051 | 1.323 | 1.4 |
| 33 | 60 | 0.415 | 26.36 | 75.115 | 15.115 | 3.806 | 1.909 | 1.661 | 1.072 | 1.6 |
| 34 | 60 | 0.453 | 23.765 | 83.315 | 23.315 | 5.871 | 2.945 | 2.562 | 1.653 | 2.4 |
| 35 | 45 | 0.455 | 17.702 | 83.891 | 38.891 | 9.793 | 4.912 | 4.274 | 2.757 | 3.4 |
| 36 | 64.8 | 0.467 | 24.697 | 86.587 | 21.787 | 5.486 | 2.752 | 2.394 | 1.545 | 1.6 |
| 37 | 54 | 0.467 | 20.546 | 86.732 | 32.732 | 8.242 | 4.134 | 3.597 | 2.321 | 2.8 |
| 38 | 50.4 | 0.475 | 18.77 | 88.61 | 38.21 | 9.621 | 4.826 | 4.199 | 2.709 | 3.4 |
| 39 | 50 | 0.475 | 18.601 | 88.704 | 38.704 | 9.746 | 4.888 | 4.254 | 2.744 | 4 |
| 40 | 55.8 | 0.475 | 20.747 | 88.753 | 32.953 | 8.298 | 4.162 | 3.622 | 2.336 | 2.8 |
| 41 | 50 | 0.483 | 18.189 | 90.714 | 40.714 | 10.252 | 5.142 | 4.475 | 2.887 | 4.2 |
| 42 | 50.4 | 0.496 | 17.648 | 94.242 | 43.842 | 11.039 | 5.537 | 4.818 | 3.108 | 4 |
| 43 | 45 | 0.498 | 15.685 | 94.677 | 49.677 | 12.509 | 6.274 | 5.46 | 3.522 | 4 |
| 44 | 54 | 0.499 | 18.764 | 94.971 | 40.971 | 10.316 | 5.175 | 4.503 | 2.905 | 3.6 |
| 45 | 60 | 0.503 | 20.638 | 95.939 | 35.939 | 9.049 | 4.539 | 3.95 | 2.548 | 3.6 |
| Mean | 54.427 | 0.465 | 20.954 | 86.681 | 32.254 | 8.122 | 4.074 | 3.545 | 2.287 | 2.893 |

TABLE 5

Group 3 patients. In this group, patients receive a higher dose by more than 10% than the calculated RxRSI. Adjustments to dose on these patients sometimes were set to a minimum dose of 50 Gy.

| PatientID | Actual dose | RSI | GARD | RxRSI minimum set to 50 Gy | RxRSI | Actual vs RxRSI min 50 Gy Dose Δ | Actual vs RxRSI Dose Δ | Mean Esophageal Decrease @ RxRSI | Mean Left Lung Decrease @ RxRSI | Mean Right Lung Decrease @ RxRSI | Mean Heart Decrease @ RxRSI | Decrease number treatment weeks (rounded up to whole fraction) |
|---|---|---|---|---|---|---|---|---|---|---|---|---|
| 1 | 59.4 | 0.015 | 124.775 | 50 | 15.71 | 9.4 | 43.69 | 2.367 | 1.187 | 1.033 | 0.666 | 1.6 |
| 2 | 59.4 | 0.092 | 70.758 | 50 | 27.703 | 9.4 | 31.697 | 2.367 | 1.187 | 1.033 | 0.666 | 1.6 |
| 3 | 60 | 0.118 | 64.117 | 50 | 30.881 | 10 | 29.119 | 2.518 | 1.263 | 1.099 | 0.709 | 1 |
| 4 | 70 | 0.166 | 62.947 | 50 | 36.698 | 20 | 33.302 | 5.036 | 2.526 | 2.198 | 1.418 | 2 |
| 5 | 66 | 0.177 | 57.198 | 50 | 38.078 | 16 | 27.922 | 4.029 | 2.021 | 1.758 | 1.134 | 1.6 |
| 6 | 50 | 0.16 | 45.875 | 50 | 35.967 | 0 | 14.033 | 0 | 0 | 0 | 0 | 1.6 |
| 7 | 50 | 0.168 | 44.588 | 50 | 37.006 | 0 | 12.994 | 0 | 0 | 0 | 0 | 1 |
| 8 | 54 | 0.198 | 43.788 | 50 | 40.696 | 4 | 13.304 | 1.007 | 0.505 | 0.44 | 0.284 | 1 |
| 9 | 60 | 0.238 | 43.028 | 50 | 46.016 | 10 | 13.984 | 2.518 | 1.263 | 1.099 | 0.709 | 1 |
| 10 | 60 | 0.239 | 42.907 | 50 | 46.146 | 10 | 13.854 | 2.518 | 1.263 | 1.099 | 0.709 | 1 |
| 11 | 60 | 0.248 | 41.802 | 50 | 47.366 | 10 | 12.634 | 2.518 | 1.263 | 1.099 | 0.709 | 2 |
| 12 | 70 | 0.304 | 41.671 | 55.435 | 55.435 | 14.565 | 14.565 | 3.668 | 1.84 | 1.601 | 1.033 | 1 |
| 13 | 60 | 0.254 | 41.159 | 50 | 48.106 | 10 | 11.894 | 2.518 | 1.263 | 1.099 | 0.709 | 2 |
| 14 | 70 | 0.323 | 39.564 | 58.387 | 58.387 | 11.613 | 11.613 | 2.924 | 1.467 | 1.276 | 0.823 | 1 |
| 15 | 54 | 0.239 | 38.621 | 50 | 46.141 | 4 | 7.859 | 1.007 | 0.505 | 0.44 | 0.284 | 1 |
| Mean | 60.187 | 0.196 | 53.52 | 50.921 | 40.689 | 9.265 | 19.498 | 2.333 | 1.17 | 1.018 | 0.657 | 1.36 |

Finally, in Group 3 patients (15/60), the radiotherapy dose prescribed was higher than the estimated RxRSI with a mean dose difference of 19.5 Gy Table 5), suggesting an opportunity for iso-curative personalized dose de-escalation. However, since some of the proposed RxRSI prescription doses fall below the clinically acceptable range (below 50 Gy), a dose of 50 Gy was re-assigned to all patients with an RxRSI<50 Gy. With this adjustment the mean dose difference was 9.27 Gy. In summary, only a quarter (15/60) of the patients received the RxRSI through the empiric radiotherapy dose approach that we use every day in the clinic. A personalized approach could have delivered the biologically-optimized RxRSI to an additional 30 patients in the cohort without the need to dose-escalate beyond acceptable, safe doses within the current standard of care for this clinical situation. The remaining 15 patients, who could not be optimized with dose escalation within SOC, could be excellent candidates for clinical trials. In conclusion, the dose prescribed and the RxRSI did not match by a clinically significant degree for 75% of the cohort patients suggesting a large opportunity for optimization both by personalized dose escalation and de-escalation.

Personalized RT Dose Prescription is Feasible without Impacting Risk of Normal Tissue Toxicity Any cytotoxic therapy, including radiation, can act as a double edged sword. Not only does its judicious application result in beneficial oncologic effects, but it also results in normal tissue toxicity. Therefore, any under or over-dosing results in either sub-optimal oncologic effect or greater than needed normal tissue complications, which can also affect quality of life and survival. To quantify this, the impact of personalized dose adjustment on normal tissue was calculated for the patients in the clinical cohort using the linear model generated from the genomic radiation plans (FIG. 5).

In Group 3 patients (patients who received higher doses than RxRSI), adjustment to the RxRSI (set to a minimum dose of 50 Gy) would have resulted in an overall mean dose decrease to the esophagus, right and left lung and heart (Tables 3, 4). In Group 2a patients (patients who received lower doses than RxRSI), adjustment to the RxRSI would have resulted in a mean increase in dose to normal tissue. The estimated increase in mean esophageal, right lung, left lung and heart dose is 2.43 Gy, 1.22 Gy, 1.06 Gy and 0.68 Gy, respectively. The mean increase in normal tissue dose for group 2a patients (RxRSI>Dose received) is very similar to mean decreases experienced by group 3 patients (RxRSI<Dose received). Thus, since Group 1 and 2b patients are not adjusted (group 1 RxRSI=Dose received and group 2b RxRSI is above SOC range), the overall risk profile for normal tissue complications for the whole population is not expected to be affected by the dose adjustments proposed by RxRSI.

Finally, the impact of dose adjustments on the risk of normal tissue complications was estimated. As shown in Table 6, patients who received a higher dose than their RxRSI (group 3) were potentially exposed to additional risks including a major coronary event (5.1%), pneumonitis (0.6%) and esophagitis (0.2%). In Group 2a patients, where RxRSI was within standard of care but higher than the empirical dose received, dose adjustment would have increased the risk of these toxicities for these patients by a similar magnitude.

treated empirically to a dose from 50-70 Gy. Patients that are biologically optimized by achieving a GARD of 33, maximize their outcome at a 5 year pLC that approximates 80%.

To validate the precision RxRSI model, the model was tested as to whether it would predict the confounding results observed in RTOG 0617, a recent Phase 3 clinical trial that compared 60 Gy to 74 Gy and carboplatin and taxol vs. carbo, taxol and cetuximab in patients with NSCLC. As shown in FIG. 2B, the precision RxRSI model predicts that uniform dose escalation to 74 Gy to unselected patients would result in no radiation-associated overall gains when compared to 60 Gy, consistent with the results observed in the actual clinical trial. To further understand the biological underpinnings to explain this result, the proportion of patients that were expected to derive a benefit from dose escalation to 74 Gy were determined. As shown in FIG. 2C, 41.3% of the patients achieved GARD 33 at 60 Gy. An additional 16.2% reached the GARD target at 74 Gy. However, the model predicted that still about 42.5% of the patients may need higher doses (>74Gy). Thus, in an unselected population, uniform dose escalation to 74 Gy benefits only a minority of patients and exposes the majority of patients to additional toxicity, obfuscating any radiation-associated clinical gains. Finally, as shown in FIG. 2D, the precision RxRSI model correctly predicts the 1-year and 2-year local control observed in RTOG 0617.

Optimizing RT Dose Using the RxRSI-Precision Model Shows Significant Potential to Improve Radiation-Associated Clinical Outcome in Lung Cancer To quantify the clinical opportunity provided by personalized RT prescription dose, in-silico clinical trials utilizing the precision RxRSI model were performed. Thus, it was analyzed whether assigning 60 or 74 Gy to patients based on their RxRSI would improve the outcome for the whole

TABLE 6

Estimating the impact of personalized dose adjustements (RxRSI) on normal tissue risk

|  | esophagus Δ dose | esophagitis | Left lung Δ dose | radiation pneumonitis | right lung Δ dose | radiation pneumonitis | heart Δ dose | Risk of major coronary event |
|---|---|---|---|---|---|---|---|---|
| Group 2A | −2.438 | −0.2% | −1.223 | −0.7% | −1.064 | −0.6% | −0.687 | −5.1% |
| Group 2B | −8.122 | −1.5% | −4.074 | −2.9% | −3.545 | −2.2% | −2.287 | −16.9% |
| Group 3 | 2.333 | 0.2% | 1.17 | 0.7% | 1.018 | 0.5% | 0.657 | 4.9% |

Figure 3:
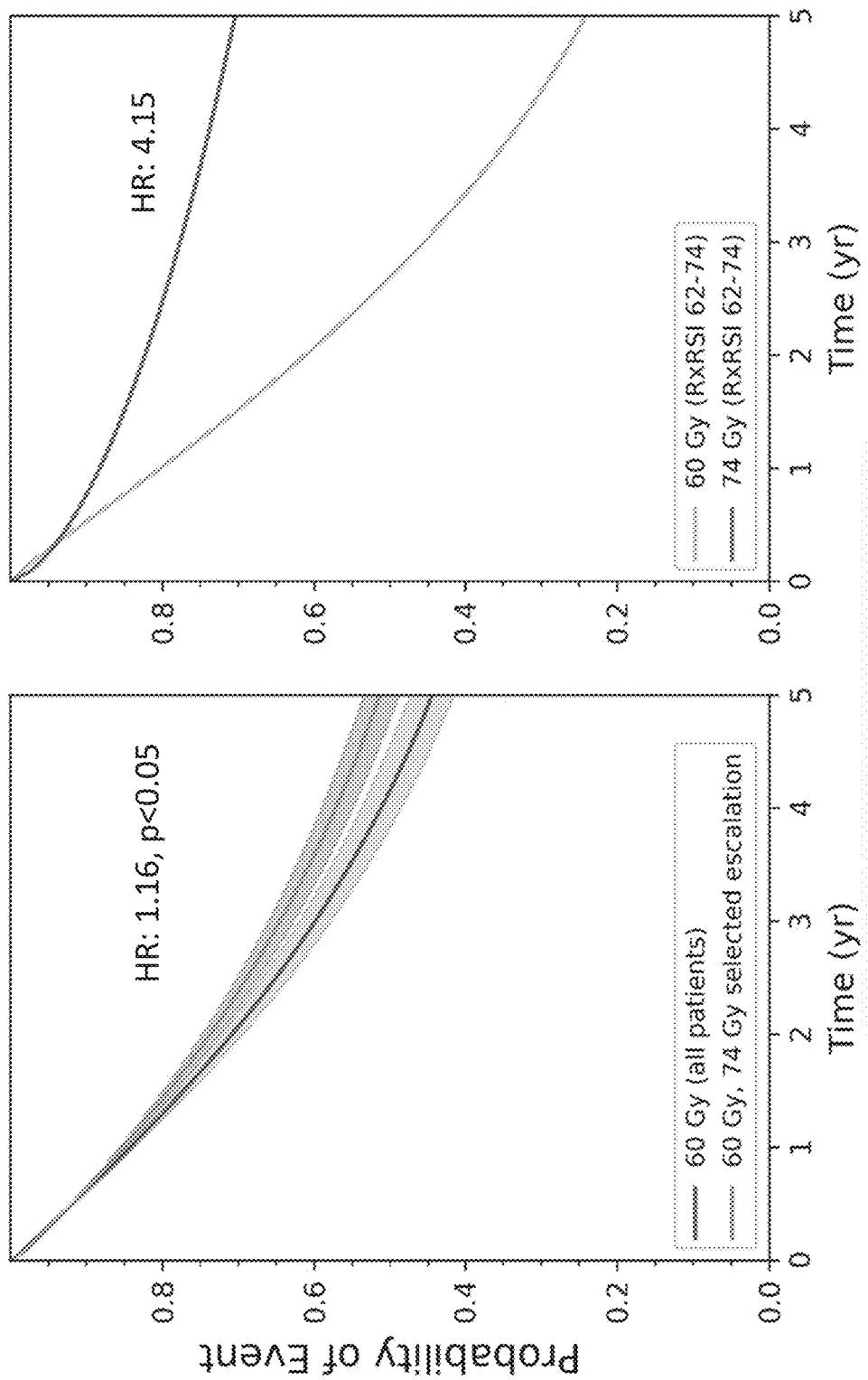
FIG. 3 shows that optimizing RT dose using the RxRSI-precision model shows significant potential to improve the radiation-associated clinical outcome in lung cancer. (A) shows average outcome of 0126 vs. genomically-guided 60 or 74. (B) shows the impact of 74 Gy in a sub-group with RxRSI 62-74.

A Personalized Radiation Dose Model Predicts the Failure of Unselected Empiric RT Dose Escalation in Lung Cancer To estimate the clinical potential for personalized prescription RT dose, a model was built to quantify the impact of optimal RT dose on local control and toxicity in the lung cancer clinical cohort (precision RxRSI model). GARD was utilized as the parameter to define biologically optimal dose (RxRSI), where clinical outcome (local control) is optimized when the GARD threshold (GARD=33) is achieved. In addition, the model incorporates a relative penalization scheme based on the added toxicity to which patients are potentially exposed when their RxRSI is exceeded. The model output is pLC (penalized local control), which includes local recurrence and events related to RT-related toxicity, but does not account for death due to other causes or disease progression. This model is a radiation outcome specific model. As shown in FIG. 2A, the precision RxRSI model reproduced the observed local control in the Moffitt lung cancer cohort when the cohort is dichotomized by GARD and the average local control for the cohort when cohort. The hypothesis is that only a subset of patients derives benefit from dose escalation to 74 Gy. Therefore, in this strategy all patients were assigned 60 Gy, except the patients with an RxRSI between 62-74 Gy. As shown in FIG. 3A, this strategy would significantly improve the predicted radiation-associated outcome for the cohort (HR1.16, p<0.05). When the cohort of patients with RxRSI 62-74 were analyzed independently, a large difference in radiation-associated outcome was predicted for the genomically-guided dose escalation (HR, 4.15). In contrast, the rest of the patients in the cohort derived no benefit from escalating the dose to 74 Gy (FIG. 3B).

DISCUSSION

In this disclosure, a clinically-feasible system to personalize RT prescription based on biological parameters and for improving clinical outcomes inherent in personalized RT for patients with NSCLC are presented. Personalized RT prescription is based on three parameters: 1. RSI which defines the patient's individual tumor radiosensitivity, 2. GARD, which defines the individualized clinical effect of a given dose of RT in a given patient with a distinct RSI and 3. RxRSI, or biologically-optimal RT prescription dose, which we define as the prescription dose required to achieve a GARD target value associated with improved clinical outcome. Personalized RT prescription provides an alternative to the empiric-based one-size fits all approach that is currently standard in the field.

The personalized genomics-based RT prescription system demonstrates that prescribing uniform, empiric-based RT dose is biologically imprecise, with 75% of patients receiving non-optimal doses of RT. Conversely, it is shown that the personalized, RxRSI-based prescription approach can deliver optimal doses to up to 75% of the patients in the clinical cohort even when a dose range is restricted within the standard of care. And this can be achieved without an overall increase in expected normal tissue toxicity for the whole cohort. To quantify the clinical potential of personalized RT prescription and to improve outcomes in lung cancer, a novel methodology that combines the biological optimization of tumor dose based on RSI/GARD and the individualized impact on normal tissue toxicity of the personalized dose adjustment was developed. The precision RxRSI model assumes an ideal biological dose to maximize tumor control and estimates outcome based on whether the RxRSI is achieved. In addition, it incorporates a penalization scheme based on the added toxicity to which patients are potentially exposed when their RxRSI is exceeded.

To validate the precision RxRSI model, the model was tested using published data from RTOG-0617, a Phase 3 randomized trial in lung cancer that assessed whether a uniform 14 Gy dose escalation would result in clinical gains in lung cancer. The precision RxRSI model correctly predicts both qualitatively and quantitatively the trial outcome: that uniform, empiric dose escalation to 74 Gy does not result in any radiation-associated clinical gains, and is secondary to the potential gains in tumor control being outweighed by the number of patients exposed to additional toxicity. However, a personalized strategy to deliver 74 Gy only to the patient subset most likely to benefit (RxRSI 62-74 Gy), would have improved the radiation-associated outcome for the whole cohort by 6.3%. Thus, it is proposed that the delivery of biologically inaccurate RT doses results in a significant detriment of clinical outcome for lung cancer patients treated with RT.

While the classic LQ model predicts that every individual in a population has the same opportunity to benefit from uniform dose escalation, the precision RxRSI model predicts that only a minority of patients (16.2% in this analysis) have the opportunity to benefit from dose escalation to 74 Gy. This opportunity to benefit is outweighed by the potential increase in toxicity to the rest of the patients. Inspecting the distribution of RSI in the two cohorts for lung cancer also illustrates an interesting point. Dose escalation from 45-60Gy results in capturing the major share of the patients in the first peak of the distribution. However, escalation from 60-74Gy only captures the tail of the first mode, and does not affect the second peak. This explains how uniform dose escalation to 60Gy shows benefit to the entire population, as the benefit outweighs the harm. In addition, the precision RxRSI model postulates that 42% of the patients are still undertreated at 74 Gy, which is consistent with the local failure rate reported in 0617. It is postulated that the distributions measured here are conserved, and further analysis of them in different disease sites could provide insight into opportunities for personalized dose escalation and de-escalation. On the strength of this analysis, it is submitted that our lack of understanding of biological heterogeneity, and how to treat it, explains the failure of biologically naïve uniform dose escalation.

The system to personalize RT prescription disclosed herein has a number of advantages over the current empiric approach. First, it accounts for biological heterogeneity that is specific to RT, updating the naive assumption of homogeneous biology across patients, which is inherent in the empiric approach. Second, since it uses biological information to formulate an optimized and personalized RT prescription dose, it requires that genomic data be collected for every patient. This provides the framework to identify novel biology that impacts RT benefit. Thus the precision RxRSI model is only the first step towards a more efficient and optimal approach to RT prescription. In contrast, multiple Phase 3 clinical trials have demonstrated that additional clinical benefit from the empiric approach is unlikely. Critically, this novel personalized system can be utilized within the standard of care framework for RT dose. Thus, clinicians can start using the precision RxRSI model and their clinical judgement to decide a biology-based RT dose for their patients without venturing outside safe, and recommended prescription doses.

While significant interest has been focused on the development of better therapeutic agents including targeted agents and immunotherapy, RT remains a fundamental curative treatment for the majority of patients with cancer. It has been estimated that 40% of all cancer cures are due to RT. In contrast, to date, no targeted agent or immunotherapy has shown similar curative potential in solid tumors. Shifting to a biology-based system will provide a new direction for radiation oncology with multiple opportunities to improve clinical outcome. And that opportunity is not small. Approximately, 50% of all cancer patients receive RT which translates to about 850,000 patients in the US. A moderate improvement in RT-based cures of 5% would represent an additional 42,500 patients potentially being cured. According to the American Cancer Society, this is approximately the same number of patients that die from breast cancer every year in the US.

In conclusion, radiation oncology has employed an empiric uniform approach to prescribe RT that is based on models developed and published over 70 years ago. It is demonstrated that this one-size fits all approach is biologically inaccurate for the majority of patients, and results in significant detriment of clinical outcome for patients treated with RT. A new paradigm is proposed, where the field updates its assumptions by acknowledging the biologically heterogeneity of tumors and moves towards the delivery of biological optimal doses of RT.

What is claimed is:

1. A method of calculating a personalized radiation therapy dosage for a subject, the method comprising:
    determining expression levels of one or more signature genes from a subject's tumor sample;
    applying a linear regression model to the gene expression levels and assigning a radiation sensitivity index (RSI) to the subject's tumor sample;
    calculating a personalized radiation dosage (RxRSI) for the subject based at least in part on a pre-determined genomic adjusted radiation dose (GARD) value and the RSI;
    calculating dosimetric parameters for normal tissues of the subject for a plurality of potential RxRSI values;
    calculating relative risk for potential RxRSI values of the plurality of potential RxRSI values; and selecting the RxRSI value of the subject from the plurality of potential RxRSI values based at least in part on the relative risk.

2. The method of claim 1, wherein determining the expression levels of one or more signature genes comprises determining the expression levels of genes selected from androgen receptor (AR); jun oncogene (c-Jun); signal transducer and activator of transcription 1 (STAT1); protein kinase C, beta (PKC); V-rel reticuloendotheliosis viral oncogene homolog A (RELA or p65); c-Ab1 oncogene 1 (c-Ab1); small ubiquitin-like modifier 1 (SUMO1); p21 activated kinase-2 (PAK2); histone deacetylase 1 (HDAC1); interferon regulatory factor 1 (IRF1); and combinations thereof.

3. The method of claim 1, wherein the tumor sample is from a subject suffering from cancer.

4. The method of claim 3, wherein the cancer is selected from colorectal cancer, breast cancer, ovarian cancer, pancreatic cancer, head and neck cancer, bladder cancer, liver cancer, renal cancer, melanoma, gastrointestinal cancer, prostate cancer, small cell lung cancer, non small cell lung cancer, sarcoma, glioblastoma, T-cell lymphoma, B-cell lymphoma, endometrial cancer, and cervical cancer.

5. The method of claim 1, where the pre-determined GARD value is based at least in part on a plurality of GARD values for subjects in a cohort.

6. The method of claim 1, further comprising:
determining a dose limiting structure of the normal tissues based at least in the dosimetric parameters.

7. The method of claim 1, further comprising:
calculating an approximate mean dose to the normal tissues based at least in part on a linear regression of the dosimetric parameters.

8. A method of treating a subject having a tumor, the method comprising:
determining expression levels of one or more signature genes from a subject's tumor sample;
applying a linear regression model to the gene expression levels and assigning a radiation sensitivity index (RSI) to the subject's tumor sample;
calculating a personalized radiation dosage (RxRSI) for the subject based at least in part on a pre-determined genomic adjusted radiation dose (GARD) value and the RSI;
calculating dosimetric parameters for normal tissues of the subject for a plurality of potential RxRSI values;
calculating relative risk for potential RxRSI values of the plurality of potential RxRSI values;
selecting the RxRSI value of the subject from the plurality of potential RxRSI values based at least in part on the relative risk; and
administering the personalized radiation dosage (RxRSI) to the subject.

9. The method of claim 8, wherein determining the expression levels of one or more signature genes comprises determining the expression levels of genes selected from androgen receptor (AR); jun oncogene (c-Jun); signal transducer and activator of transcription 1 (STAT1); protein kinase C, beta (PKC); V-rel reticuloendotheliosis viral oncogene homolog A (RELA or p65); c-Ab1 oncogene 1 (c-Ab1); small ubiquitin-like modifier 1 (SUMO1); p21 activated kinase-2 (PAK2); histone deacetylase 1 (HDAC1); interferon regulatory factor 1 (IRF1); and combinations thereof.

10. The method of claim 8, wherein the tumor sample is from a subject suffering from cancer.

11. The method of claim 10, wherein the cancer is selected from colorectal cancer, breast cancer, ovarian cancer, pancreatic cancer, head and neck cancer, bladder cancer, liver cancer, renal cancer, melanoma, gastrointestinal cancer, prostate cancer, small cell lung cancer, non small cell lung cancer, sarcoma, glioblastoma, T-cell lymphoma, B-cell lymphoma, endometrial cancer, and cervical cancer.

12. A system for developing a personalized radiation therapy treatment plan for a subject having a tumor, comprising:
a processor; and
a memory operably coupled to the processor, the memory having computer-executable instructions stored thereon that, when executed by the processor, cause the processor to:
determine a radiation sensitivity index (RSI) of the tumor from expression levels of one or more signature genes in the tumor;
calculate a personalized radiation dosage (RxRSI) for the subject based at least in part on a pre-determined genomic adjusted radiation dose (GARD) value and the RSI;
calculate normal tissue toxicity of the personalized radiation dosage;
calculate dosimetric parameters for normal tissues of the subject for a plurality of potential RxRSI values;
calculate relative risk for potential RxRSI values of the plurality of potential RxRSI values;
select the RxRSI value of the subject from the plurality of potential RxRSI values based at least in part on the relative risk; and
provide the personalized radiation therapy treatment plan for the subject.

13. The system of claim 12, wherein determining the radiation sensitivity index (RSI) of the tumor comprises:
determining expression levels of one or more signature genes from the subject's tumor; and
applying a linear regression model to the gene expression levels and determining the radiation sensitivity index (RSI) of the tumor.

14. The system of claim 13, wherein determining the expression levels of one or more signature genes comprises determining the expression levels of genes selected from androgen receptor (AR); jun oncogene (c-Jun); signal transducer and activator of transcription 1 (STAT1); protein kinase C, beta (PKC); V-rel reticuloendotheliosis viral oncogene homolog A (RELA or p65); c-Ab1 oncogene 1 (c-Ab1); small ubiquitin-like modifier 1 (SUMO1); p21 activated kinase-2 (PAK2); histone deacetylase 1 (HDAC1); interferon regulatory factor 1 (IRF1); and combinations thereof.

15. The system of claim 12, wherein the subject's tumor is a cancer tumor selected from colorectal cancer, breast cancer, ovarian cancer, pancreatic cancer, head and neck cancer, bladder cancer, liver cancer, renal cancer, melanoma, gastrointestinal cancer, prostate cancer, small cell lung cancer, non-small cell lung cancer, sarcoma, glioblastoma, T-cell lymphoma, B-cell lymphoma, endometrial cancer, and cervical cancer.

16. The system of claim 12, further comprising a memory having computer-executable instructions stored thereon that, when executed by the processor, cause the processor to provide a standard radiation therapy treatment plan based on empiric dosing.

17. A computer-implemented method for minimizing the risk of radiation therapy comprising:
obtaining a radiation sensitivity index (RSI) of a subject's tumor from expression levels of one or more signature genes in the tumor;

calculating a personalized radiation dosage (RxRSI) for the subject based at least in part on a pre-determined genomic adjusted radiation dose (GARD) value;
calculating normal tissue toxicity of the personalized radiation dosage;
calculating dosimetric parameters for normal tissues of the subject for a plurality of potential RxRSI values;
calculating relative risk for potential RxRSI values of the plurality of potential RxRSI values;
selecting the RxRSI value of the subject from the plurality of potential RxRSI values based at least in part on the relative risk; and
providing a personalized radiation therapy treatment plan for the subject.

18. The method of claim 1, wherein the pre-determined GARD value is based on an improved outcome in a cancer type associated with the subject's tumor sample.

19. The method of claim 1, wherein the pre-determined GARD value is based on empiric values in a cancer type associated with the subject's tumor sample.

20. The method of claim 1, wherein the pre-determined GARD value dependent on cancer type.

21. A method of calculating a personalized radiation therapy dosage for a subject, the method comprising:
determining expression levels of one or more signature genes from a subject's tumor sample;
applying a linear regression model to the gene expression levels and assigning a radiation sensitivity index (RSI) to the subject's tumor sample; and
calculating a personalized radiation dosage (RxRSI) for the subject based at least in part on a pre-determined genomic adjusted radiation dose (GARD) value and the RSI, wherein the pre-determined GARD value is about 33 for non-small cell lung cancer.

22. A method of treating a subject having a tumor, the method comprising:
determining expression levels of one or more signature genes from a subject's tumor sample;
applying a linear regression model to the gene expression levels and assigning a radiation sensitivity index (RSI) to the subject's tumor sample;
calculating a personalized radiation dosage (RxRSI) for the subject based at least in part on a pre-determined genomic adjusted radiation dose (GARD) value and the RSI; and
administering the calculated personalized radiation dosage (RxRSI) to the subject, wherein the pre-determined GARD value is about 33 for non-small cell lung cancer.

23. A system for developing a personalized radiation therapy treatment plan for a subject having a tumor, comprising:
a processor; and
a memory operably coupled to the processor, the memory having computer-executable instructions stored thereon that, when executed by the processor, cause the processor to:
determine a radiation sensitivity index (RSI) of the tumor from expression levels of one or more signature genes in the tumor;
calculate a personalized radiation dosage (RxRSI) for the subject based at least in part on a pre-determined genomic adjusted radiation dose (GARD) value and the RSI;
calculate normal tissue toxicity of the personalized radiation dosage; and
provide the personalized radiation therapy treatment plan for the subject, wherein the pre-determined GARD value is about 33 for non-small cell lung cancer.

24. A computer-implemented method for minimizing the risk of radiation therapy comprising:
obtaining a radiation sensitivity index (RSI) of a subject's tumor from expression levels of one or more signature genes in the tumor;
calculating a personalized radiation dosage (RxRSI) for the subject based at least in part on a pre-determined genomic adjusted radiation dose (GARD) value;
calculating normal tissue toxicity of the personalized radiation dosage; and
providing a personalized radiation therapy treatment plan for the subject, wherein the pre-determined GARD value is about 33 for non-small cell lung cancer.

* * * * *